US011759498B2

(12) United States Patent
Jeong et al.

(10) Patent No.: US 11,759,498 B2
(45) Date of Patent: Sep. 19, 2023

(54) COMPOSITION FOR DIAGNOSING ALLERGIES TO MITES, METHOD OF DIAGNOSING ALLERGIES TO MITES, AND COMPOSITION FOR PREVENTING OR TREATING ALLERGIES TO MITES

(71) Applicant: Industry-Academic Cooperation Foundation, Yonsei University, Seoul (KR)

(72) Inventors: Kyoung Yong Jeong, Seoul (KR); Kyung Hee Park, Seoul (KR); Jung Won Park, Seoul (KR); Chang Ook Park, Seoul (KR); Kwang Hoon Lee, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 168 days.

(21) Appl. No.: 17/307,289

(22) Filed: May 4, 2021

(65) Prior Publication Data

US 2021/0268065 A1    Sep. 2, 2021

Related U.S. Application Data

(62) Division of application No. 16/138,357, filed on Sep. 21, 2018, now abandoned.

(30) Foreign Application Priority Data

Sep. 22, 2017    (KR) ........................ 10-2017-0122870

(51) Int. Cl.
| | | |
|---|---|---|
| A61K 38/17 | (2006.01) | |
| A61P 37/08 | (2006.01) | |
| A61K 39/35 | (2006.01) | |
| G01N 33/53 | (2006.01) | |
| G01N 33/68 | (2006.01) | |

(52) U.S. Cl.
CPC .......... *A61K 38/1767* (2013.01); *A61K 39/35* (2013.01); *A61P 37/08* (2018.01); *G01N 33/53* (2013.01); *G01N 33/686* (2013.01); *G01N 33/6893* (2013.01); *G01N 2333/43582* (2013.01); *G01N 2800/24* (2013.01)

(58) Field of Classification Search
None
See application file for complete search history.

(56) References Cited

U.S. PATENT DOCUMENTS

| 5,314,991 A | 5/1994 | Oka |
| 2014/0010845 A1 | 1/2014 | Brimnes |
| 2016/0151481 A1 | 6/2016 | Webster |

FOREIGN PATENT DOCUMENTS

| EP | 0473111 A2 | 3/1992 |
| KR | 10-2013-0118884 | 10/2013 |
| KR | 10-2013-0121806 | 11/2013 |
| WO | 2016/193126 A1 | 12/2016 |

OTHER PUBLICATIONS

Wu Y.-L., Jiang C.-L., Liu Z.-G.; "Cloning, expression, purification and immunological activity of genes from Dermatophagoides farinae."; Submitted (Jun. 2014) to the EMBL/GenBank/DDBJ databases.*
Kristiansen et al. 'Allergen immunotherapy for the prevention of allergy: A systematic review and meta-analysis.' Pediatr Allergy Immunol. Feb. 2017;28(1):18-29. doi: 10.1111/pai.12661. Epub Dec. 12, 2016.*
Martignago et al. 'Preventive actions of allergen immunotherapy: the facts and the effects in search of evidence.' Clin Mol. Allergy 2017; 15: 13. Published online Jun. 15, 2017. doi: 10.1186/s12948-017-0070-7.*
Erban et al. 'Proteogenomics of the house dust mite, Dermatophagoides farinae: Allergen repertoire, accurate allergen identification, isoforms, and sex-biased proteome differences.' J. Proteom. 210(2020) 103535 https://doi.org/10.1016/j.jprot.2019.103535.*
http://allergen.org/search.php?allergensource=farinae&searchsource= Search printed Jun. 13, 2023.*
Karlin et al., "Applications and statistics for multiple high-scoring segments in molecular sequences", Proc. Natl. Acad. Sci. USA, vol. 90, pp. 5873-5877, Jun. 1993; 5 pages.
Pearson, "Rapid and Sensitive Sequence Comparison with FASTP and FASTA" Methods in Enzymology, vol. 183 (1990), pp. 63-98.
Lee et al. 'Protein sequence analysis of a novel 103-kDaDermatophagoides pteronyssinusmite allergen and prevalence of serum immunoglobulin E reactivity to rDer p. 11 in allergic adult patients.' Clin Exp Allergy 34:354-362, 2004.
Valenta et al. 'The recombinant allergen-based concept of componentresolved diagnostics and immunotherapy (CRD and CRIT).' Clin. Exp. Allerg., 29:896-904, 1999.
Chan et al. 'Nuclear Magnetic Resonance Structure-Based Epitope Mapping and Modulation of Dust Mite Group 13 Allergen as a Hypoallergen.' J. Immunol.176 (8) 4852-4860, 2006.
Ong ST "Expressed Sequence tags analysis of major allergens producing dust mites and molecular characterization of their allergens" A thesis submitted for the degree of doctor of philosophy department of paediatrics National University of Singapore 2003.
Allergen.org Der p. 32 submission 2014.

(Continued)

*Primary Examiner* — Nora M Rooney
(74) *Attorney, Agent, or Firm* — Schwabe Williamson & Wyatt

(57) ABSTRACT

Mite proteins according to an aspect may be used in diagnosing allergic diseases. Results of diagnosing allergic diseases by using the proteins have high reliability and validity. Further, the proteins may be used in a composition for preventing or treating allergic diseases.

6 Claims, 8 Drawing Sheets

Specification includes a Sequence Listing.

(56) References Cited

OTHER PUBLICATIONS

Dilworth et al. 'Sequence analysis of cDNA coding for a major house dust mite allergen, Der fl.' Clin. Exp. Allerg. 21:25-32, 1991.
Non-Final Office Action for U.S. Appl. No. 16/138,357 dated Sep. 11, 2019, 15 pgs.
Final Office Action for U.S. Appl. No. 16/138,357 dated Mar. 20, 2020, 17 pgs.
Non-Final Office Action for U.S. Appl. No. 16/138,357 dated Jul. 29, 2020, 16 pgs.
Final Office Action for U.S. Appl. No. 16/138,357 dated Sep. 11, 2019, 18 pgs.
Calderon et al., 'Respiratory allergy caused by house dust mites: What do we really know?', J Allergy Clin Immunolvolume, 2014, vol. 136, pp. 38-48.
Thomas et al., 'Hierarchy and molecular properties of house dust mite allergens', Allergology International, 2015, vol. 64, pp. 304-311.
Jeong et al., 'Profiles of IgE Sensitization to Der f 1, Der f 2, Der f 6, Der f 8, Der f 10, and Der f 20 in Korean House Dust Mite Allergy Patients', Allergy Asthma Immunology Research, 2015, vol. 7, pp. 483-488.
An et al., 'Dermatophagoides farinae Allergens Diversity Identification by Proteomics', Molecular & Cellular Proteomics, 2013, vol. 12, pp. 1818-1828.

* cited by examiner

SEQUENCE LISTING

<160> NUMBER OF SEQ ID NOS: 41

<210> SEQ ID NO 1
<211> LENGTH: 876
<212> TYPE: PRT
<213> ORGANISM: Artificial Sequence
<220> FEATURE:
<223> OTHER INFORMATION: Der f 11

<400> SEQUENCE: 1

Met Ser Ala Arg Thr Ala Lys Tyr Met Tyr Arg Ser Ser Gly Ala Gly
1               5                   10                  15

Ala Ser Gly Asp Ile Ser Val Glu Tyr Gly Thr Asp Leu Gly Ala Leu
            20                  25                  30

Thr Arg Leu Glu Asp Lys Ile Arg Leu Leu Ser Asp Asp Leu Glu Ser
        35                  40                  45

Glu Arg Glu Met Arg Gln Arg Ile Glu Arg Glu Lys Ala Glu Leu Gln
    50                  55                  60

Ile Gln Val Met Ser Leu Gly Glu Arg Leu Glu Glu Ala Glu Gly Ser
65                  70                  75                  80

Ser Glu Ser Val Thr Glu Met Asn Lys Lys Arg Asp Ser Glu Leu Ala

```
                        85                  90                  95
Lys Leu Arg Lys Leu Leu Glu Asp Val His Ile Glu Ser Glu Glu Thr
            100                 105                 110
Ala His His Leu Arg Gln Lys His Gln Ala Ala Ile Gln Glu Met Gln
            115                 120                 125
Asp Gln Leu Asp Gln Leu Gln Lys Ala Lys Asn Lys Ser Asp Lys Glu
            130                 135                 140
Lys Gln Lys Phe Gln Ala Glu Val Phe Glu Leu Leu Ala Gln Leu Glu
145                 150                 155                 160
Thr Ala Asn Lys Glu Lys Leu Thr Ala Leu Lys Asn Val Glu Lys Leu
            165                 170                 175
Glu Tyr Thr Val His Glu Leu Asn Ile Lys Ile Glu Glu Ile Asn Arg
            180                 185                 190
Thr Val Ile Glu Leu Thr Ser His Lys Gln Arg Leu Ser Gln Glu Asn
            195                 200                 205
Thr Glu Leu Ile Lys Glu Val His Glu Val Lys Leu Gln Leu Asp Asn
            210                 215                 220
Ala Asn His Leu Lys Thr Gln Ile Ala Gln Gln Leu Glu Asp Thr Arg
225                 230                 235                 240
His Arg Leu Glu Glu Glu Arg Lys Arg Ala Ser Leu Glu Asn His
            245                 250                 255
Ala His Thr Leu Glu Val Glu Leu Glu Ser Leu Lys Val Gln Leu Asp
            260                 265                 270
Glu Glu Ser Glu Ala Arg Leu Glu Leu Glu Arg Gln Leu Thr Lys Ala
            275                 280                 285
Asn Gly Asp Ala Ala Ser Trp Lys Ser Lys Tyr Glu Ala Glu Leu Gln
            290                 295                 300
Ala His Ala Asp Glu Val Glu Glu Leu Arg Arg Lys Met Ala Gln Lys
305                 310                 315                 320
Ile Ser Glu Tyr Glu Glu Gln Leu Glu Ala Leu Leu Asn Lys Cys Ser
            325                 330                 335
Ser Leu Glu Lys Gln Lys Ser Arg Leu Gln Ser Glu Val Glu Val Leu
            340                 345                 350
Ile Met Asp Leu Glu Lys Ala Thr Ala His Ala Gln Leu Glu Lys
            355                 360                 365
Arg Val Ala Gln Leu Glu Lys Ile Asn Leu Asp Leu Lys Asn Lys Leu
            370                 375                 380
Glu Glu Val Thr Met Leu Met Glu Gln Ala Gln Lys Glu Leu Arg Val
385                 390                 395                 400
Lys Ile Ala Glu Leu Gln Lys Leu Gln His Glu Tyr Glu Lys Leu Arg
            405                 410                 415
Asp Gln Arg Asp Gln Leu Ala Arg Glu Asn Lys Lys Leu Thr Asp Asp
            420                 425                 430
Leu Ala Glu Ala Lys Ser Gln Leu Asn Asp Ala His Arg Arg Ile His
            435                 440                 445
Glu Gln Glu Ile Glu Ile Lys Arg Leu Glu Asn Glu Arg Asp Glu Leu
            450                 455                 460
Ser Ala Ala Tyr Lys Glu Ala Glu Thr Leu Arg Lys Gln Glu Glu Ala
465                 470                 475                 480
Lys Asn Gln Arg Leu Ile Ala Glu Leu Ala Gln Val Arg His Asp Tyr
            485                 490                 495
Glu Lys Arg Leu Ala Gln Lys Asp Glu Glu Ile Glu Ala Leu Arg Lys
            500                 505                 510
```

Gln Tyr Gln Ile Glu Ile Glu Gln Leu Asn Met Arg Leu Ala Glu Ala
            515                 520                 525

Glu Ala Lys Leu Lys Thr Glu Ile Ala Arg Leu Lys Lys Tyr Gln
530                 535                 540

Ala Gln Ile Thr Glu Leu Glu Leu Ser Leu Asp Ala Ala Asn Lys Ala
545                 550                 555                 560

Asn Ile Asp Leu Gln Lys Thr Ile Lys Gln Ala Leu Gln Ile Thr
            565                 570                 575

Ala Glu Leu Gln Ala His Tyr Asp Glu Val His Arg Gln Leu Gln Gln
            580                 585                 590

Ala Val Asp Gln Leu Gly Val Thr Gln Arg Arg Cys Gln Ala Leu Gln
            595                 600                 605

Ala Glu Leu Glu Glu Met Arg Ile Ala Leu Glu Gln Ala Asn Arg Ala
            610                 615                 620

Lys Arg Gln Ala Glu Gln Leu His Glu Glu Ala Val Val Arg Val Asn
625                 630                 635                 640

Glu Leu Thr Thr Ile Asn Val Asn Leu Ala Ser Ala Lys Ser Lys Leu
                645                 650                 655

Glu Ser Glu Phe Ser Ala Leu Gln Ala Asp Tyr Asp Glu Val His Lys
            660                 665                 670

Glu Leu Arg Ile Ser Asp Glu Arg Val Gln Lys Leu Thr Ile Glu Leu
            675                 680                 685

Lys Ser Thr Lys Asp Leu Leu Ile Glu Glu Gln Glu Arg Leu Val Lys
            690                 695                 700

Leu Glu Thr Val Lys Lys Ser Leu Glu Gln Glu Val Arg Thr Leu His
705                 710                 715                 720

Val Arg Ile Glu Glu Val Glu Ala Asn Ala Leu Ala Gly Gly Lys Arg
                725                 730                 735

Val Ile Ala Lys Leu Glu Ser Arg Ile Arg Asp Val Glu Ile Glu Val
            740                 745                 750

Glu Glu Glu Arg Arg Arg His Ala Glu Thr Asp Lys Met Leu Arg Lys
            755                 760                 765

Lys Asp His Arg Val Lys Glu Leu Leu Leu Gln Asn Glu Glu Asp His
770                 775                 780

Lys Gln Ile Gln Leu Leu Gln Glu Met Thr Asp Lys Leu Asn Glu Lys
785                 790                 795                 800

Val Lys Val Tyr Lys Arg Gln Met Gln Glu Gln Gly Met Ser Gln
            805                 810                 815

Gln Asn Leu Thr Arg Val Arg Arg Phe Gln Arg Glu Leu Glu Ala Ala
            820                 825                 830

Glu Asp Arg Ala Asp Gln Ala Glu Ser Asn Leu Ser Phe Ile Arg Ala
            835                 840                 845

Lys His Arg Ser Trp Val Thr Thr Ser Gln Val Pro Gly Gly Thr Arg
850                 855                 860

Gln Val Phe Thr Thr Gln Glu Glu Thr Thr Asn Tyr
865                 870                 875

<210> SEQ ID NO 2
<211> LENGTH: 2631
<212> TYPE: DNA
<213> ORGANISM: Artificial Sequence
<220> FEATURE:
<223> OTHER INFORMATION: Der f 11

<400> SEQUENCE: 2

```
atgtcggcac gtacagctaa atatatgtac cgatccagtg gtgctggtgc ctctggtgat    60
atttccgttg aatatggtac cgatttaggt gccttaactc gacttgagga caaaatccga   120
ttgttatccg atgatttgga atccgaacgt gaaatgcgac aacgtatcga acgtgaaaag   180
gccgaattac agatccaagt gatgagcctt ggtgaacgtt tagaagaggc cgaaggatca   240
agcgaaagtg ttaccgaaat gaacaaaaaa agagattccg aattggcaaa attgagaaaa   300
ttgttggaag atgttcacat tgaatcggaa gaaacggccc atcatttgcg acagaaacat   360
caggctgcca tccaggaaat gcaagatcaa cttgaccaat gcaaaaagc gaaaaataaa   420 tcggataaag agaagcaaaa atttcaggct gaagttttg aattattagc tcaattggaa   480
acggccaata aggaaaaatt aacggcattg aaaaatgtag aaaaattgga atataccgta   540
catgaattga atatcaaaat cgaagaaatc aaccgtacgg tcattgaatt aacatcacat   600
aaacaacgtt taagtcagga gaataccgaa ttgatcaaag aagttcacga agttaaatta   660
caattggaca atgcaaacca tttgaagaca cagattgccc aacaattaga agacactcga   720
catcgtttgg aagaagagga acgaaaacgt gccagtctcg aaaatcatgc ccatacattg   780
gaagtggaat tagaatcatt gaaagtacaa ttggacgaag aatccgaggc tcgtcttgag   840
cttgaacgtc aattgaccaa agccaatggc gatgctgcat catggaagtc caaatacgaa   900
gctgaattgc aagcacatgc cgatgaagtt gaagaacttc gtcgtaaaat ggctcaaaag   960
atttcggaat acgaagaaca attggaagcc ttattgaata aatgcagttc attggagaaa  1020
caaaaatctc gacttcaaag cgaagttgaa gttttgatta tggatcttga aaaagcgaca  1080
gcacatgcac aacaattaga aaaacgtgtt gctcaattgg aaaagattaa tcttgatttg  1140
aagaataaat tggaagaggt taccatgttg atggaacaag cacagaaaga acttcgagtc  1200
aagattgctg aattacagaa attgcaacat gaatatgaaa aattacgtga tcaacgtgat  1260
caattggcac gtgaaaacaa gaaacttaca gacgatcttg ccgaagctaa atcacaattg  1320
aacgatgctc accgtagaat ccatgaacaa gaaattgaaa tcaaacgatt agagaatgaa  1380
cgtgatgaat tatcggctgc ctataaagaa gcagaaacat tgagaaaaca agaagaggcc  1440
aaaaatcaac gattgattgc cgaattggca caggtacgac atgattatga aaaacgtttg  1500
gcacaaaaag atgaagaaat tgaagcattg cgcaaacaat atcaaattga aattgaacaa  1560
cttaacatgc gattggccga ggctgaagct aaactcaaga ccgaaattgc acgattgaag  1620
aaaaaatacc aggcacagat taccgaattg gaattgtcat ggatgcagc caataaggct  1680 aatatcgatt tgcaaaagac tattaaaaaa caagctcttc aaattacggc ggagctccaa  1740
gcacattatg atgaagttca tcgtcaattg caacaagcag tggatcaatt gggtgttaca  1800
caacgacgat gccaagcatt gcaagccgaa ttggaagaga tgcgtattgc attggaacag  1860
gctaatcgtg ctaaaagaca agccgaacaa ttgcatgaag aagctgttgt acgtgttaac  1920
gaacttacca caattaacgt caatttggca tcggctaaaa gtaaattgga atcagaattc  1980
tctgcacttc aagctgatta cgatgaagta cataaagaac ttagaatttc tgatgaacga  2040
gtacagaaac ttacaattga actcaaatct actaaagatt tgttgatcga agaacaagaa  2100
cgattggtta aattggaaac agtgaaaaaa tcattggaac aagaggtacg aacattgcat  2160
gtccgtattg aagaggtcga agccaatgca ttggccggtg gtaaacgtgt cattgccaaa  2220
ttggaaagcc gaattcgtga tgttgaaatt gaagttgaag aagaacgacg acgacatgcc  2280
gaaacggaca aaatgttacg taaaaaggat catcgtgtca aggaattgtt gttgcaaaat  2340
```

```
gaggaggacc ataaacaaat tcaattgcta caggaaatga ctgataaatt gaatgaaaag    2400
gtcaaagttt acaaacgaca gatgcaagaa caggagggaa tgagccaaca gaatttgaca    2460
cgtgtcagac gattccaacg tgaattggaa gcagccgaag atcgtgccga tcaagctgaa    2520
tcgaacttat cgttcattcg tgctaaacat cgttcatggg ttaccacaag ccaggttcca    2580
ggcggtaccc gacaagtgtt cacgacgcaa gaagaaacaa ccaattatta a             2631
```

```
<210> SEQ ID NO 3
<211> LENGTH: 131
<212> TYPE: PRT
<213> ORGANISM: Artificial Sequence
<220> FEATURE:
<223> OTHER INFORMATION: Der f 13

<400> SEQUENCE: 3

Met Ala Ser Ile Glu Gly Lys Tyr Lys Leu Glu Lys Ser Glu Lys Phe
1               5                   10                  15

Asp Glu Phe Leu Asp Lys Leu Gly Val Gly Phe Met Val Lys Thr Ala
            20                  25                  30

Ala Lys Thr Leu Lys Pro Thr Phe Glu Val Ala Ile Glu Asn Asp Gln
        35                  40                  45

Tyr Ile Phe Arg Ser Leu Ser Thr Phe Lys Asn Thr Glu Ala Lys Phe
    50                  55                  60

Lys Leu Gly Glu Glu Phe Glu Glu Asp Arg Ala Asp Gly Lys Arg Val
65                  70                  75                  80

Lys Thr Val Ile Gln Lys Glu Gly Asp Asn Lys Phe Val Gln Thr Gln
                85                  90                  95

Phe Gly Asp Lys Glu Val Lys Ile Ile Arg Glu Phe Asn Gly Asp Glu
            100                 105                 110

Val Val Val Thr Ala Ser Cys Asp Gly Val Thr Ser Val Arg Thr Tyr
        115                 120                 125

Lys Arg Ile
    130
```

```
<210> SEQ ID NO 4
<211> LENGTH: 396
<212> TYPE: DNA
<213> ORGANISM: Artificial Sequence
<220> FEATURE:
<223> OTHER INFORMATION: Der f 13

<400> SEQUENCE: 4
atggcaagca ttgaaggtaa atataaattg gaaaaatcgg aaaaattcga tgaatttctc      60
gacaaattgg gcgtcggttt tatggtgaaa acggcagcta aacattgaa accaacattt      120 gaagtggcaa ttgaaaatga ccaatacatt ttccgttcat taagtacgtt caaaaatact    180
gaagctaaat tcaaattggg cgaagaattc gaagaagatc gtgccgatgg taaacgagtg    240
aaaacggtca tccaaaaaga aggtgacaat aaatttgttc aaacacaatt cggtgataaa    300
gaagtgaaaa ttattcgtga attcaatggc gatgaagttg ttgtgactgc atcctgtgat    360
ggtgtcactt ccgttcgaac atataaacga atctaa                              396
```

```
<210> SEQ ID NO 5
<211> LENGTH: 341
<212> TYPE: PRT
<213> ORGANISM: Artificial Sequence
<220> FEATURE:
<223> OTHER INFORMATION: Der f 14
```

<400> SEQUENCE: 5

```
Phe Val Met Lys Arg Glu Pro Leu Arg Phe Arg Asp Ile Thr Val Glu
1               5                   10                  15
Gly Asn Glu Asn Ala Tyr Ile Lys Asn Gly Lys Leu His Leu Ser Leu
            20                  25                  30
Met Asp Pro Ser Thr Leu Ser Leu Val Thr Lys Ala Asp Gly Lys Ile
        35                  40                  45
Asp Met Thr Val Asp Leu Ile Ser Pro Val Thr Lys Arg Ala Ser Leu
    50                  55                  60
Lys Ile Asp Ser Lys Lys Tyr Asn Leu Phe His Glu Gly Leu Ser
65                  70                  75                  80
Ala Ser Ile Val Asn Pro Arg Leu Ser Trp His Gln Tyr Thr Lys Arg
                85                  90                  95
Asp Ser Arg Glu Tyr Lys Ser Asp Val Glu Leu Ser Leu Arg Ser Ser
            100                 105                 110
Asp Ile Ala Leu Lys Ile Thr Met Pro Asp Tyr Asn Ser Lys Ile His
        115                 120                 125
Tyr Ser Arg Gln Gly Asp Gln Ile Asn Met Asp Ile Asp Gly Thr Leu
    130                 135                 140
Ile Glu Gly His Ala Gln Gly Thr Ile Arg Glu Gly Lys Ile His Ile
145                 150                 155                 160
Lys Gly Arg Gln Thr Asp Phe Glu Ile Glu Ser Asn Tyr Arg Tyr Glu
                165                 170                 175
Asp Gly Lys Leu Ile Ile Glu Pro Val Lys Ser Glu Asn Gly Lys Leu
            180                 185                 190
Glu Gly Val Leu Ser Arg Lys Val Pro Ser His Leu Thr Leu Glu Thr
        195                 200                 205
Pro Arg Val Lys Met Asn Met Lys Tyr Asp Arg Tyr Ala Pro Val Lys
    210                 215                 220
Val Phe Lys Leu Asp Tyr Asp Gly Ile His Phe Glu Lys His Thr Asp
225                 230                 235                 240
Ile Glu Tyr Glu Pro Gly Val Arg Tyr Lys Ile Ile Gly Asn Gly Lys
                245                 250                 255
Leu Lys Asp Asp Gly Arg His Tyr Ser Ile Asp Val Gln Gly Ile Pro
            260                 265                 270
Arg Lys Ala Phe Asn Leu Asp Ala Asp Leu Met Asp Phe Lys Leu Lys
        275                 280                 285
Val Ser Lys Pro Glu Asp Ser Asn Lys Ala Gln Phe Ser Tyr Thr Phe
    290                 295                 300
Asn Glu Tyr Thr Glu Thr Glu Tyr Glu Phe Asp Pro His Arg Ala
305                 310                 315                 320
Tyr Tyr Val Asn Trp Leu Ser Ser Ile Arg Lys Tyr Ile Gln Asn Phe
                325                 330                 335
Ile Val Glu Asp Asn
            340
```

<210> SEQ ID NO 6
<211> LENGTH: 1144
<212> TYPE: DNA
<213> ORGANISM: Artificial Sequence
<220> FEATURE:
<223> OTHER INFORMATION: Der f 14

<400> SEQUENCE: 6

```
tttgtcatga aacgagaacc attgcgattc agagacatca ctgtcgaagg aaacgaaaat    60
```

-continued

```
gcctatatca aaaatggcaa acttcatttg tcgcttatgg atccgtcaac attgagttta      120
gtcacgaaag ccgatggaaa aatcgacatg acagtagact tgatatcgcc agtcacaaaa      180
cgtgcatcgt tgaaaattga ttcaaagaaa tacaacctttt ccatgaagg tgaattgagt      240 gcatcgatcg taaacccacg attgtcatgg catcaataca cgaaacgcga ttctcgtgaa      300
tacaagagtg atgtagaact atcgttgcga tcgtcggaca ttgctctcaa gattacgatg      360
cctgattata attcgaaaat tcattattca cgacaaggtg atcaaatcaa catggacatc      420
gatggtacat tgatcgaagg tcatgcacaa ggaaccatca gagaaggtaa aatccacatt      480
aaaggtagac aaactgattt cgagatcgaa tccaactacc gatacgaaga tggcaaacta      540
atcatcgaac cggtcaagag tgaaaatggc aaattggaag gcgttctttc ccgtaaggtg      600
ccatcacatc tgcacactag aacaccacga gtcaagatga atatgaaata tgatcgatat      660
gcaccagtca aagtgttcaa attggattat gatggcatcc acttcgagaa atacgat     720 attgaatacg aacctggcgt tcgatacaag atcatcggca atggaaaact caaggatgat      780
ggccgccact attctatcga tgtgcaaggt attccacgca aagcattcaa tctggacgct      840
gacttgatgg atttcaaact gaaagtgagc aagccagaag atagcaataa agctcaattc      900
agctacacat tcaacgaata taccgagacc gaagaatatg aattcgatcc acatcgtgcc      960
tattatgtta attggttgag ttccattcgc aaatacatcc agaatttcat cgtcgaagac     1020
aactgaacac cattaatgca cattgattga aatgcaatg agcaaatgtc ttcattgatt     1080
cattcgatta ttccattctc taattttat atctattgac ttgtaataaa atctaaagga     1140
aaac                                                                 1144
```

<210> SEQ ID NO 7
<211> LENGTH: 296
<212> TYPE: PRT
<213> ORGANISM: Artificial Sequence
<220> FEATURE:
<223> OTHER INFORMATION: Der f 32

<400> SEQUENCE: 7

Met Ser Thr Thr Asn Tyr Ser Val Asp His Arg Gly Ser Phe Asn Ser
1               5                   10                  15

Leu Asp Tyr Arg Ile Tyr Phe Lys Asp Asn Ser Asn Gly Lys Ile Ile
                20                  25                  30

Ser Pro Trp His Asp Ile Pro Leu Phe Val Asp Lys Ser Ala Lys His
            35                  40                  45

Tyr Asn Met Val Val Glu Ile Pro Arg Trp Thr Asn Glu Lys Met Glu
        50                  55                  60

Ile Ala Thr Ala Glu Pro Met Ser Pro Ile Lys Gln Asp Ile Lys Lys
65                  70                  75                  80

Gly Ala Leu Arg Tyr Val Lys Asn Val Phe Pro His Lys Gly Tyr Ile
                85                  90                  95

Trp Asn Tyr Gly Ala Phe Pro Gln Thr Trp Glu Asn Pro Asn His Ile
            100                 105                 110

Asp Gln Asp Thr Lys Thr Lys Gly Asp Asn Asp Pro Ile Asp Val Ile
        115                 120                 125

Glu Ile Gly Ser Arg Val Ala Lys Arg Gly Asp Val Val Pro Val Lys
    130                 135                 140

Ile Leu Gly Thr Ile Ala Leu Ile Asp Glu Gly Glu Thr Asp Trp Lys
145                 150                 155                 160

```
Ile Ile Ala Ile Asp Thr Arg Asp Glu Leu Ala Ser Gln Met Asn Asn
            165                 170                 175

Val Asp Asp Val Glu Lys Leu Leu Pro Gly Leu Leu Arg Ala Thr Val
        180                 185                 190

Glu Trp Phe Lys Ile Tyr Lys Ile Pro Asp Gly Lys Pro Ala Asn Lys
    195                 200                 205

Phe Ala Phe Asn Gly Glu Ala Lys Asp Arg Glu Phe Ala Glu Lys Ile
210                 215                 220

Val Glu Glu Thr His Gln Tyr Trp Gln Glu Met Met Glu Asn Lys Ser
225                 230                 235                 240

Gly Glu His Lys Leu Asp Leu Lys Asn Val Thr Leu Gly Asn Ser Phe
            245                 250                 255

Ser Ile Asn Asp Glu Gln Ala Lys Gln Phe Leu Glu Thr Arg Pro Ser
        260                 265                 270

Ser Asp Ala Val Glu Pro Thr Pro Ile Ala Asp Gln Val Ala Ile Asp
    275                 280                 285

Lys Trp His His Val Lys Leu Ile
    290                 295

<210> SEQ ID NO 8
<211> LENGTH: 891
<212> TYPE: DNA
<213> ORGANISM: Artificial Sequence
<220> FEATURE:
<223> OTHER INFORMATION: Der f 32

<400> SEQUENCE: 8
atgtctacta caaattattc tgttgatcat cgtggttcct ttaattctct tgattatcgt      60
atttatttca agataatag caatggaaag ataattagtc cttggcacga tatcccattg      120
tttgtcgata atcggccaa acattacaat atggttgttg aaattccacg ctggactaat      180
gaaaaaatgg aaattgctac tgccgaacca atgtccacca ttaaacaaga cataaaaaaa      240
ggtgcattac gttatgtgaa aaatgtttc cctcataaag gttacatatg gaattatggt      300
gcatttccac aaacatggga aaatccgaat catattgatc aagacactaa aacaaaaggc      360
gataatgatc caattgatgt gattgaaatt ggatcacgtg ttgctaaacg tggtgatgtc      420
gtaccggtaa aaatactcgg aacaattgca ttgatcgatg aaggtgaaac tgattggaaa      480
atcatcgcta ttgatacacg tgatgaattg gcctcccaaa tgaataatgt tgatgatgtt      540
gaaaaattat acccggctt acttcgagct acagttgaat ggtttaaaat ttataaaata      600
cctgatggta aaccggcaaa taatttgcc tttaatggtg aagctaaaga tcgtgaattt      660
gctgaaaaaa tcgttgaaga aacacatcaa tattggcaag aaatgatgga aaacaaatcc      720
ggtgaacata aattggattt gaaaaatgta actttgggta ttcattttc gatcaatgat      780 gaacaagcaa aacaattttt ggaaacacga ccatctagtg atgctgttga accaacacca      840
attgctgatc aagtggccat cgataaatgg catcatgtta aattgatcta a               891

<210> SEQ ID NO 9
<211> LENGTH: 490
<212> TYPE: PRT
<213> ORGANISM: Artificial Sequence
<220> FEATURE:
<223> OTHER INFORMATION: Der f Alt a 10

<400> SEQUENCE: 9

Met Ala Gln Val Glu Val Lys Tyr Thr Gln Ile Phe Ile Asn Asn Glu
1               5                   10                  15
```

```
Trp His Asp Ser Ile Ser Gly Lys Thr Phe Glu Thr Ile Asn Pro Phe
             20                  25                  30

Thr Glu Glu Lys Leu Ala Asn Val Gln Glu Gly Asp Lys Ala Asp Ile
         35                  40                  45

Asp Arg Ala Val Val Ala Val Asp Ala Phe Arg Phe Asp Ser Pro
 50                  55                  60

Trp Arg Gln Met Asp Ala Ser Gln Arg Gly His Leu Leu Tyr Arg Leu
 65              70                  75                      80

Ala Asp Leu Ile Glu Arg Asp Gln Asp Tyr Ile Ala Ser Leu Glu Ser
                 85                  90                  95

Met Asp Asn Gly Lys Pro Lys Thr Met Ala Leu Phe Asp Val Asp Leu
             100                 105                 110

Ala Ile Lys Val Phe Arg Tyr Tyr Ala Gly Tyr Ala Asp Lys Ile His
         115                 120                 125

Gly Lys Thr Ile Pro Ala Asp Gly Lys Val Phe Ala Phe Thr Arg Ile
 130                 135                 140

Glu Pro Val Gly Ile Cys Gly Gln Ile Val Pro Trp Asn Phe Pro Phe
145                 150                 155                 160

Leu Met Ala Ser Trp Lys Phe Gly Pro Ala Leu Cys Ala Gly Asn Thr
                 165                 170                 175

Val Val Leu Lys Pro Ala Glu Gln Thr Pro Leu Ser Ala Leu Tyr Leu
             180                 185                 190

Ala Ser Leu Thr Lys Glu Gly Gly Phe Pro Pro Gly Val Val Asn Val
         195                 200                 205

Val Pro Gly Phe Gly Glu Thr Ala Gly Ala Ala Leu Val Asp Asn Pro
 210                 215                 220

Lys Val Asp Lys Ile Ala Phe Thr Gly Ser Thr Glu Ile Gly Lys Leu
225                 230                 235                 240

Ile Met Arg Asn Gly Ser His Ser Met Lys Arg Ile Thr Leu Glu Leu
                 245                 250                 255

Gly Gly Lys Ser Pro Leu Val Val Thr Glu Asn Val Glu Asp Ile Ala
             260                 265                 270

Gln Ala Ala Arg Thr Ala Gln Asp Ser Cys Phe Leu Asn Met Gly Gln
         275                 280                 285

Cys Cys Cys Ala Gly Thr Arg Thr Phe Val His Glu Ser Ile Tyr Asp
290                 295                 300

Glu Phe Val Lys His Ser Val Glu Tyr Cys Gln Ser His Val Phe Gly
305                 310                 315                 320

Asn Pro Phe Asp Ser Lys Thr Ala Phe Gly Pro Gln Val Asp Lys Ile
                 325                 330                 335

Gln Met Asn Arg Ile Leu Glu Met Ile Glu Ser Gly Lys Gln Glu Gly
             340                 345                 350

Ala Arg Cys Val Ala Gly Gly Asn Arg Met Asp Lys Arg Gly Tyr Phe
         355                 360                 365

Val Glu Pro Thr Val Phe Ala Asp Val Thr Asp Gly Met Arg Ile Ala
 370                 375                 380

Arg Glu Glu Ile Phe Gly Pro Val Gln Gln Ile Leu Lys Tyr Lys Thr
385                 390                 395                 400

Leu Asp Glu Val Ile Glu Arg Cys Asn Asp Thr Asn Tyr Gly Leu Gly
                 405                 410                 415

Ser Ala Ile Leu Thr Asn Asp Ile Asn Glu Ala Met Lys Phe Ser Arg
                 420                 425                 430
```

```
              Ser Ile Arg Ala Gly Ser Val Trp Ile Asn Ile Pro Tyr Met Ile Pro
                              435                 440                 445

Val Ser Val Gln Thr Pro Phe Gly Gly Phe Lys Glu Ser Gly Val Gly
                      450                 455                 460

Arg Glu Leu Gly Glu Asp Gly Leu Arg Gly Tyr Gly Glu Ile Lys Thr
              465                 470                 475                 480

Val Val Ile Met Asp Arg Glu Lys Lys Met
                              485                 490

<210> SEQ ID NO 10
<211> LENGTH: 1597
<212> TYPE: DNA
<213> ORGANISM: Artificial Sequence
<220> FEATURE:
<223> OTHER INFORMATION: Der f Alt a 10

<400> SEQUENCE: 10
aaaattcgaa ataccatggc ccaagtggaa gtaaaatata ctcagatttt catcaacaat      60
gaatggcacg attcgattag tggtaaaaca ttcgaaacaa tcaatccatt tactgaggaa     120
aaattggcca atgtacaaga gggtgataaa gccgatatag atcgtgctgt tgttgcggct     180
gttgatgcat ttcgttttga ttcaccatgg cgacagatgg atgcatcaca acgtggtcat     240
ctgctatatc gtcttgctga tcttattgaa agagatcaag attatattgc tagcctggaa     300
agtatggata atggtaaacc aaaaacaatg gcattgttcg atgttgattt ggccatcaaa     360
gtttttcgtt attatgccgg ttatgctgat aaaattcatg gtaaaaccat tccagcagat     420
ggcaaagtgt tcgcttttac acgaattgaa cctgttggta tttgtggtca aatcgttccg     480 tggaatttc cgttttaat ggctagttgg aaatttggac cagcattgtg tgccggaaat     540
accgtcgtat tgaaaccagc tgaacagaca ccgttaagcg ctctatattt ggccagttta     600
actaaagaag gtggatttcc acccggtgtg gtcaatgtgg tacctggttt cggtgaaaca     660
gccggtgcag ctttagttga taatccaaaa gtcgataaaa ttgctttcac tggttcaacg     720
gaaatcggta aattaatcat gcgaaatggt tcacattcaa tgaaacgaat cacactggaa     780
ttgggtggta aatcaccatt ggtagtaact gaaaatgttg aagatattgc acaagctgca     840
cgtacagcac aagattcatg tttcctgaat atgggccaat gttgttgtgc cggtacccga     900
acatttgttc atgaatcaat ctatgatgaa tttgttaaac attcagtgga atattgtcag     960
tcacatgtat ttggcaatcc attcgattca aaaactgcat tcggtccaca agtggataaa    1020
atccagatga atcgaatact tgaaatgatt gaatctggta acaggaagg tgcccgttgt    1080 gttgccggtg gtaatcgtat ggataaacgt ggatatttcg ttgaaccaac tgtttttgcc    1140
gatgttaccg atgggatgcg aaattgcacgt gaagaaattt ttggtccagt acaacagatt    1200
cttaaatata aaacactgga tgaagttatt gaacgttgta atgatacaaa ttatggtcta    1260
ggatcggcta tactcaccaa tgatattaat gaagcaatga aattttcacg tagtattcgt    1320
gctggttccg tttggatcaa tataccatac atgataccgg ttagtgtaca aacaccattc    1380
ggtggtttca agaaagtgg tgttggccgc gaacttggtg aagatggtct tcgtggttat    1440
ggtgaaatta aaactgttgt cattatggat cgtgaaaaga aatgtaaag aaaaaccgaa    1500 aaaaaaaatt tttcctatttt caacaaacag ttgaaatata tccattttat ccagaataaa    1560
aattcgaatt taaattagaa aaaaaaaaaa aaaaaa                              1597

<210> SEQ ID NO 11
<211> LENGTH: 321
```

```
<212> TYPE: PRT
<213> ORGANISM: Artificial Sequence
<220> FEATURE:
<223> OTHER INFORMATION: Der f 1

<400> SEQUENCE: 11

Met Lys Phe Val Leu Ala Ile Ala Ser Leu Leu Val Leu Ser Thr Val
1               5                   10                  15

Tyr Ala Arg Pro Ala Ser Ile Lys Thr Phe Glu Glu Phe Lys Lys Ala
            20                  25                  30

Phe Asn Lys Asn Tyr Ala Thr Val Glu Glu Glu Val Ala Arg Lys
        35                  40                  45

Asn Phe Leu Glu Ser Leu Lys Tyr Val Glu Ala Asn Lys Gly Ala Ile
    50                  55                  60

Asn His Leu Ser Asp Leu Ser Leu Asp Glu Phe Lys Asn Arg Tyr Leu
65                  70                  75                  80

Met Ser Ala Glu Ala Phe Glu Gln Leu Lys Thr Gln Phe Asp Leu Asn
                85                  90                  95

Ala Glu Thr Ser Ala Cys Arg Ile Asn Ser Val Asn Val Pro Ser Glu
            100                 105                 110

Leu Asp Leu Arg Ser Leu Arg Thr Val Thr Pro Ile Arg Met Gln Gly
        115                 120                 125

Gly Cys Gly Ser Cys Trp Ala Phe Ser Gly Val Ala Ala Thr Glu Ser
130                 135                 140

Ala Tyr Leu Ala Tyr Arg Asn Thr Ser Leu Asp Leu Ser Glu Gln Glu
145                 150                 155                 160

Leu Val Asp Cys Ala Ser Gln His Gly Cys His Gly Asp Thr Ile Pro
                165                 170                 175

Arg Gly Ile Glu Tyr Ile Gln Gln Asn Gly Val Val Glu Glu Arg Ser
            180                 185                 190

Tyr Pro Tyr Val Ala Arg Glu Gln Gln Cys Arg Arg Pro Asn Ser Gln
        195                 200                 205

His Tyr Gly Ile Ser Asn Tyr Cys Gln Ile Tyr Pro Pro Asp Val Lys
210                 215                 220

Gln Ile Arg Glu Ala Leu Thr Gln Thr His Thr Ala Ile Ala Val Ile
225                 230                 235                 240

Ile Gly Ile Lys Asp Leu Arg Ala Phe Gln His Tyr Asp Gly Arg Thr
                245                 250                 255

Ile Ile Gln His Asp Asn Gly Tyr Gln Pro Asn Tyr His Ala Val Asn
            260                 265                 270

Ile Val Gly Tyr Gly Ser Thr Gln Gly Val Asp Tyr Trp Ile Val Arg
        275                 280                 285

Asn Ser Trp Asp Thr Thr Trp Gly Asp Ser Gly Tyr Gly Tyr Phe Gln
290                 295                 300

Ala Gly Asn Asn Leu Met Met Ile Glu Gln Tyr Pro Tyr Val Val Ile
305                 310                 315                 320

Met

<210> SEQ ID NO 12
<211> LENGTH: 1081
<212> TYPE: DNA
<213> ORGANISM: Artificial Sequence
<220> FEATURE:
<223> OTHER INFORMATION: Der f 1

<400> SEQUENCE: 12
```

```
tttttttttt ttttttttcca tcaaaattaa aaattcatca aaaatgaaat tcgttttggc      60
cattgcctct ttgttggtat tgagcactgt ttatgctcgt ccagcttcaa tcaaaacttt     120
tgaagaattc aaaaaagcct tcaacaaaaa ctatgccacc gttgaagagg aagaagttgc     180
ccgtaaaaac tttttggaat cattgaaata tgttgaagct aacaaaggtg ccatcaacca     240
tttgtccgat ttgtcattgg atgaattcaa aaaccgttat ttgatgagtg ctgaagcttt     300
tgaacaactc aaaactcaat tcgatttgaa tgccgaaaca agcgcttgcc gtatcaattc     360
ggttaacgtt ccatcggaat tggatttacg atcactgcga actgtcactc caatccgtat     420
gcaaggaggc tgtggttcat gttgggcttt ctctggtgtc gccgcaactg aatcagctta     480
tttggcctac cgtaacacgt ctttggatct ttctgaacag gaactcgtcg attgcgcatc     540
tcaacacgga tgtcacggcg atacaatacc aagaggcatc gaatacatcc aacaaaatgg     600
tgtcgttgaa gaaagaagct atccatacgt tgcacgagaa caacaatgcc gacgaccaaa     660
ttcgcaacat tacggtatct caaactactg ccaaatttat ccaccagatg tgaaacaaat     720
ccgtgaagct ttgactcaaa cacacacagc tattgccgtc attattggca ttaaagattt     780
gagagctttt caacattatg atggacgaac aatcattcaa catgacaatg gttatcaacc     840
aaactatcat gccgtcaaca ttgtcggtta cggaagtaca caaggcgtcg attattggat     900
cgtacgaaac agttgggata ctacctgggg tgatagcgga tacgatatt tccaagccgg     960 aaacaacctc atgatgatcg aacaatatcc atatgttgta atcatgtgaa catttgaaat    1020
tgaatatatt tatttgtttt caaaataaaa acaactactc ttgcgagtat tttttacttt    1080
t                                                                    1081
```

<210> SEQ ID NO 13  
<211> LENGTH: 146  
<212> TYPE: PRT  
<213> ORGANISM: Artificial Sequence  
<220> FEATURE:  
<223> OTHER INFORMATION: Der f 13

<400> SEQUENCE: 13

```
Met Ile Ser Lys Ile Leu Cys Leu Ser Leu Leu Val Ala Ala Val Val
1               5                   10                  15

Ala Asp Gln Val Asp Val Lys Asp Cys Ala Asn Asn Glu Ile Lys Lys
                20                  25                  30

Val Met Val Asp Gly Cys His Gly Ser Asp Pro Cys Ile Ile His Arg
            35                  40                  45

Gly Lys Pro Phe Thr Leu Glu Ala Leu Phe Asp Ala Asn Gln Asn Thr
        50                  55                  60

Lys Thr Ala Lys Ile Glu Ile Lys Ala Ser Leu Asp Gly Leu Glu Ile
65                  70                  75                  80

Asp Val Pro Gly Ile Asp Thr Asn Ala Cys His Phe Met Lys Cys Pro
                85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Thr Val Lys Leu Ile
        115                 120                 125

Gly Asp Asn Gly Val Leu Ala Cys Ala Ile Ala Thr His Gly Lys Ile
130                 135                 140

Arg Asp
145
```

<210> SEQ ID NO 14
<211> LENGTH: 528
<212> TYPE: DNA
<213> ORGANISM: Artificial Sequence
<220> FEATURE:
<223> OTHER INFORMATION: Der f 2

<400> SEQUENCE: 14

| | | | | |
|---|---|---|---|---|
| aaaaaaaaac aacataaccg aaaatgattt ccaaaatctt gtgcctttca ttgttggtag | | | | 60 |
| cagccgttgt tgccgatcaa gtcgatgtta aagattgtgc caacaatgaa atcaaaaaag | | | | 120 |
| taatggtcga tggttgccat ggttctgatc catgcatcat ccatcgtggt aaaccattca | | | | 180 |
| ctttggaagc cttattcgat gccaaccaaa acactaaaac cgctaaaatt gaaatcaaag | | | | 240 |
| ccagcctcga tggtcttgaa attgatgttc ccggtatcga taccaatgct tgccatttta | | | | 300 |
| tgaaatgtcc attggttaaa ggtcaacaat atgatatcaa atatacatgg aatgtgccga | | | | 360 |
| aaattgcacc aaaatctgaa acgttgtcg ttacagtcaa acttatcggt gataatggtg | | | | 420 |
| ttttggcttg cgctattgct acccatggta aaatccgtga ttaaaaaaaa ataaataaga | | | | 480 |
| aaattttcac caacatcgaa caaaattcaa taaccaaaat ttgaatcc | | | | 528 |

<210> SEQ ID NO 15
<211> LENGTH: 299
<212> TYPE: PRT
<213> ORGANISM: Artificial Sequence
<220> FEATURE:
<223> OTHER INFORMATION: Der f 10

<400> SEQUENCE: 15

Phe Phe Phe Val Ala Ala Lys Gln Gln Gln Pro Ser Thr Lys Met
1               5                   10                  15

Glu Ala Ile Lys Lys Lys Met Gln Ala Met Lys Leu Glu Lys Asp Asn
            20                  25                  30

Ala Ile Asp Arg Ala Glu Ile Ala Gln Lys Ala Arg Asp Ala Asn
        35                  40                  45

Leu Arg Ala Glu Lys Ser Glu Glu Val Arg Ala Leu Gln Lys Lys
    50                  55                  60

Ile Gln Gln Ile Glu Asn Glu Leu Asp Gln Val Gln Glu Gln Leu Ser
65                  70                  75                  80

Ala Ala Asn Thr Lys Leu Glu Glu Lys Glu Lys Ala Leu Gln Thr Ala
                85                  90                  95

Glu Gly Asp Val Ala Ala Leu Asn Arg Arg Ile Gln Leu Ile Glu Glu
            100                 105                 110

Asp Leu Glu Arg Ser Glu Glu Arg Leu Lys Ile Ala Thr Ala Lys Leu
        115                 120                 125

Glu Glu Ala Ser Gln Ser Ala Asp Glu Ser Arg Met Arg Lys Met
    130                 135                 140

Leu Glu His Arg Ser Ile Thr Asp Glu Arg Met Asp Gly Leu Glu
145                 150                 155                 160

Asn Gln Leu Lys Glu Ala Arg Met Met Ala Glu Ala Asp Arg Lys
                165                 170                 175

Tyr Asp Glu Val Ala Arg Lys Leu Ala Met Val Glu Ala Asp Leu Glu
            180                 185                 190

Arg Ala Glu Glu Arg Ala Glu Thr Gly Glu Ser Lys Ile Val Glu Leu
        195                 200                 205

Glu Glu Glu Leu Arg Val Val Gly Asn Asn Leu Lys Ser Leu Glu Val
    210                 215                 220

```
Ser Glu Glu Lys Ala Gln Gln Arg Glu Ala Tyr Glu Gln Gln Ile
225                 230                 235                 240

Arg Ile Met Thr Ala Lys Leu Lys Glu Ala Glu Ala Arg Ala Glu Phe
            245                 250                 255

Ala Glu Arg Ser Val Gln Lys Leu Gln Lys Glu Val Asp Arg Leu Glu
        260                 265                 270

Asp Glu Leu Val His Glu Lys Glu Lys Tyr Lys Ser Ile Ser Asp Glu
    275                 280                 285

Leu Asp Gln Thr Phe Ala Glu Leu Thr Gly Tyr
        290                 295

<210> SEQ ID NO 16
<211> LENGTH: 988
<212> TYPE: DNA
<213> ORGANISM: Artificial Sequence
<220> FEATURE:
<223> OTHER INFORMATION: Der f 10

<400> SEQUENCE: 16 tttttttcg ttgcagctaa acaacaacaa caaccatcaa caaaaatgga ggccatcaag        60
aaaaaaatgc aggcaatgaa gctcgagaaa gataatgcta tcgatcgagc tgaaattgcc      120
gaacaaaaag cccgtgatgc taatctacgt gccgaaaagt ctgaggaaga agttcgtgca      180
ttacagaaaa aaatccaaca aattgaaaat gaattggatc aggtccaaga caattatcg       240 gctgccaata caaaattgga ggaaaaggaa aaagccctac agaccgctga aggtgatgtt      300
gcagcattga atcgtcgtat tcaattgatt gaagaagatt tggaacgatc agaagaacga      360
cttaagattg ctacagccaa attggaagag gcatcacaat ctgccgatga atctgaacgt      420
atgcgtaaaa tgcttgaaca tcgatccatc accgatgaag aacgtatgga tggtttggaa      480
aatcaactta agaagcccg tatgatggcc gaagatgctg atagaaaata tgatgaagtt       540
gcccgtaaat tggcaatggt tgaagccgat ttgaacgtg ctgaagaacg tgccgaaacc       600
ggtgaatcga aaattgttga actcgaagaa gaattacgtg ttgtcggtaa caatctcaaa      660
tcattggaag ttagcgaaga gaaagctcaa caacgtgaag aagcctatga caacagatc       720 cgtataatga cggctaaact taagaagcc gaagcacgtg ccgaatttgc tgaacgttcg       780
gtacaaaaac tccagaaaga agtcgatcgt ttggaagacg aattggtcca cgaaaaggaa      840
aaatacaaat ccatctccga cgaattggac agacatttg ccgaacttac tggttattaa      900
taataattct ttcatattac gcagacagaa ttttcgatta ttttaacaa caccaccacc      960 accagcaaca gcaacaacga aaaatcac                                         988

<210> SEQ ID NO 17
<211> LENGTH: 171
<212> TYPE: PRT
<213> ORGANISM: Artificial Sequence
<220> FEATURE:
<223> OTHER INFORMATION: Der f 30

<400> SEQUENCE: 17

Met Ala Ala Asn Pro Glu Ser Thr Thr Lys Thr Ser Arg Val Arg Met
1               5                   10                  15

Asn Ile Gln Ile Asn Leu Glu Phe Tyr Ala Ser Tyr Val Tyr Gln Gln
            20                  25                  30

Met Ala Tyr His Phe Asn Arg Asp Asp Val Ala Leu Pro Gly Phe Glu
        35                  40                  45

Lys Phe Phe Asp Val Ser Ser Lys Glu Glu Arg Glu His Ala Glu Arg
```

```
                50              55              60
Phe Met Lys Leu Gln Asn Gln Arg Gly Gly Arg Ile Val Leu Asp Asp
 65                  70                  75                  80

Ile His Lys Pro Gln Gln Gln Asp Trp Ser Ser Gly Leu Glu Ala Met
                 85                  90                  95

Arg Ala Ala Leu Glu Leu Glu Lys Thr Val Asn Gln Ala Leu Leu Asp
            100                 105                 110

Leu His Ala Val Ala Thr Lys His Asn Asp Ala Gln Phe Ala Asp Phe
        115                 120                 125

Ile Glu Thr His Tyr Leu Thr Glu Gln Val Glu Ala Ile Lys Lys Leu
    130                 135                 140

Ala Asp Tyr Ile Thr Asn Leu Glu Arg Cys Gly Pro Gly Leu Gly Glu
145                 150                 155                 160

Tyr Leu Phe Asp Arg His Thr Leu His Ser Ser
                165                 170

<210> SEQ ID NO 18
<211> LENGTH: 516
<212> TYPE: DNA
<213> ORGANISM: Artificial Sequence
<220> FEATURE:
<223> OTHER INFORMATION: Der f 30

<400> SEQUENCE: 18
atggctgcta atcctgaatc aacaaccaaa acttcacgtg tacgaatgaa tattcaaatt        60
aatttggagt ctatgcatc ctatgtatat caacagatgg cctatcattt taatcgtgat       120
gatgttgcat tgcctggttt tgaaaaattt ttcgatgtat catccaaaga agaacgtgaa       180
cacgctgaac gttttatgaa attacagaat caacgtggtg acgtattgt attggatgat       240 attcataaac cgcaacaaca agattggtca tcaggattgg aagcaatgcg tgctgcattg       300
gaattggaaa aaacagtcaa tcaggcattg ttggatttgc atgccgttgc accaaaacac       360
aatgatgcac aatttgctga tttttattgaa acacattatc taactgaaca agtggaagcc       420
atcaagaaat ggctgattta tattaccaat ttggaacgtt gtggccccgg acttggtgaa       480
tatctttttg atcgtcatac attgcattca tcgtaa                                 516

<210> SEQ ID NO 19
<211> LENGTH: 161
<212> TYPE: PRT
<213> ORGANISM: Artificial Sequence
<220> FEATURE:
<223> OTHER INFORMATION: Der f 11 fragment

<400> SEQUENCE: 19

His Ile Glu Ser Glu Glu Thr Ala His His Leu Arg Gln Lys His Gln
  1               5                  10                  15

Ala Ala Ile Gln Glu Met Gln Asp Gln Leu Asp Gln Leu Gln Lys Ala
             20                  25                  30

Lys Asn Lys Ser Asp Lys Glu Lys Gln Lys Phe Gln Ala Glu Val Phe
         35                  40                  45

Glu Leu Leu Ala Gln Leu Glu Thr Ala Asn Lys Glu Lys Leu Thr Ala
     50                  55                  60

Leu Lys Asn Val Glu Lys Leu Glu Tyr Thr Val His Glu Leu Asn Ile
 65                  70                  75                  80

Lys Ile Glu Glu Ile Asn Arg Thr Val Ile Glu Leu Thr Ser His Lys
                 85                  90                  95
```

```
Gln Arg Leu Ser Gln Glu Asn Thr Glu Leu Ile Lys Glu Val His Glu
                100                 105                 110

Val Lys Leu Gln Leu Asp Asn Ala Asn His Leu Lys Thr Gln Ile Ala
            115                 120                 125

Gln Gln Leu Glu Asp Thr Arg His Arg Leu Glu Glu Glu Arg Lys
        130                 135                 140

Arg Ala Ser Leu Glu Asn His Ala His Thr Leu Glu Val Glu Leu Glu
145                 150                 155                 160

Ser

<210> SEQ ID NO 20
<211> LENGTH: 309
<212> TYPE: PRT
<213> ORGANISM: Artificial Sequence
<220> FEATURE:
<223> OTHER INFORMATION: Der f 14 fragment

<400> SEQUENCE: 20

Met Asp Pro Ser Thr Leu Ser Leu Val Thr Lys Ala Asp Gly Lys Ile
1               5                   10                  15

Asp Met Thr Val Asp Leu Ile Ser Pro Val Thr Lys Arg Ala Ser Leu
            20                  25                  30

Lys Ile Asp Ser Lys Lys Tyr Asn Leu Phe His Glu Gly Glu Leu Ser
        35                  40                  45

Ala Ser Ile Val Asn Pro Arg Leu Ser Trp His Gln Tyr Thr Lys Arg
    50                  55                  60

Asp Ser Arg Glu Tyr Lys Ser Asp Val Glu Leu Ser Leu Arg Ser Ser
65                  70                  75                  80

Asp Ile Ala Leu Lys Ile Thr Met Pro Asp Tyr Asn Ser Lys Ile His
                85                  90                  95

Tyr Ser Arg Gln Gly Asp Gln Ile Asn Met Asp Ile Asp Gly Thr Leu
            100                 105                 110

Ile Glu Gly His Ala Gln Gly Thr Ile Arg Glu Gly Lys Ile His Ile
        115                 120                 125

Lys Gly Arg Gln Thr Asp Phe Glu Ile Glu Ser Asn Tyr Arg Tyr Glu
    130                 135                 140

Asp Gly Lys Leu Ile Ile Glu Pro Val Lys Ser Glu Asn Gly Lys Leu
145                 150                 155                 160

Glu Gly Val Leu Ser Arg Lys Val Pro Ser His Leu Thr Leu Glu Thr
                165                 170                 175

Pro Arg Val Lys Met Asn Met Lys Tyr Asp Arg Tyr Ala Pro Val Lys
            180                 185                 190

Val Phe Lys Leu Asp Tyr Asp Gly Ile His Phe Glu Lys His Thr Asp
        195                 200                 205

Ile Glu Tyr Glu Pro Gly Val Arg Tyr Lys Ile Ile Gly Asn Gly Lys
    210                 215                 220

Leu Lys Asp Asp Gly Arg His Tyr Ser Ile Asp Val Gln Gly Ile Pro
225                 230                 235                 240

Arg Lys Ala Phe Asn Leu Asp Ala Asp Leu Met Asp Phe Lys Leu Lys
                245                 250                 255

Val Ser Lys Pro Glu Asp Ser Asn Lys Ala Gln Phe Ser Tyr Thr Phe
            260                 265                 270

Asn Glu Tyr Thr Glu Thr Glu Glu Tyr Glu Phe Asp Pro His Arg Ala
        275                 280                 285

Tyr Tyr Val Asn Trp Leu Ser Ser Ile Arg Lys Tyr Ile Gln Asn Phe
```

Ile Val Glu Asp Asn
305

<210> SEQ ID NO 21
<211> LENGTH: 321
<212> TYPE: PRT
<213> ORGANISM: Artificial Sequence
<220> FEATURE:
<223> OTHER INFORMATION: Der f 1 mutant

<400> SEQUENCE: 21

Met Lys Phe Val Leu Ala Ile Ala Ser Leu Leu Val Leu Ser Thr Val
1               5                   10                  15

Tyr Ala Arg Pro Ala Ser Ile Lys Thr Phe Glu Glu Phe Lys Lys Ala
            20                  25                  30

Phe Asn Lys Asn Tyr Ala Thr Val Glu Glu Glu Val Ala Arg Lys
        35                  40                  45

Asn Phe Leu Glu Ser Leu Lys Tyr Val Glu Ala Asn Lys Gly Ala Ile
    50                  55                  60

Asn His Leu Ser Asp Leu Ser Leu Asp Glu Phe Lys Asn Arg Tyr Leu
65                  70                  75                  80

Met Ser Ala Glu Ala Phe Glu Gln Leu Lys Thr Gln Phe Asp Leu Asn
                85                  90                  95

Ala Glu Thr Ser Ala Cys Arg Ile Asn Ser Val Asn Val Pro Ser Glu
            100                 105                 110

Leu Asp Leu Arg Ser Leu Arg Thr Val Thr Pro Ile Arg Met Gln Gly
        115                 120                 125

Gly Cys Gly Ser Cys Trp Ala Phe Ser Gly Val Ala Ala Thr Glu Ser
    130                 135                 140

Ala Tyr Leu Ala Tyr Arg Gln Thr Ser Leu Asp Leu Ser Glu Gln Glu
145                 150                 155                 160

Leu Val Asp Cys Ala Ser Gln His Gly Cys His Gly Asp Thr Ile Pro
                165                 170                 175

Arg Gly Ile Glu Tyr Ile Gln Gln Asn Gly Val Val Glu Glu Arg Ser
            180                 185                 190

Tyr Pro Tyr Val Ala Arg Glu Gln Gln Cys Arg Arg Pro Asn Ser Gln
        195                 200                 205

His Tyr Gly Ile Ser Asn Tyr Cys Gln Ile Tyr Pro Pro Asp Val Lys
    210                 215                 220

Gln Ile Arg Glu Ala Leu Thr Gln Thr His Thr Ala Ile Ala Val Ile
225                 230                 235                 240

Ile Gly Ile Lys Asp Leu Arg Ala Phe Gln His Tyr Asp Gly Arg Thr
                245                 250                 255

Ile Ile Gln His Asp Asn Gly Tyr Gln Pro Asn Tyr His Ala Val Asn
            260                 265                 270

Ile Val Gly Tyr Gly Ser Thr Gln Gly Val Asp Tyr Trp Ile Val Arg
        275                 280                 285

Asn Ser Trp Asp Thr Thr Trp Gly Asp Ser Gly Tyr Gly Tyr Phe Gln
    290                 295                 300

Ala Gly Asn Asn Leu Met Met Ile Glu Gln Tyr Pro Tyr Val Val Ile
305                 310                 315                 320

Met

<210> SEQ ID NO 22

```
<210> SEQ ID NO 22
<211> LENGTH: 27
<212> TYPE: DNA
<213> ORGANISM: Artificial Sequence
<220> FEATURE:
<223> OTHER INFORMATION: rDer f 1 primer

<400> SEQUENCE: 22
ctcgagcgtc cagcttcaat caaaact                                        27

<210> SEQ ID NO 23
<211> LENGTH: 44
<212> TYPE: DNA
<213> ORGANISM: Artificial Sequence
<220> FEATURE:
<223> OTHER INFORMATION: rDer f 1 primer

<400> SEQUENCE: 23
ggccgcttag tgatggtgat ggtgatgcgc gccgcgtgat ggtg                     44

<210> SEQ ID NO 24
<211> LENGTH: 19
<212> TYPE: DNA
<213> ORGANISM: Artificial Sequence
<220> FEATURE:
<223> OTHER INFORMATION: rDer f 2 primer

<400> SEQUENCE: 24
gatcaagtcg atgttaaag                                                 19

<210> SEQ ID NO 25
<211> LENGTH: 18
<212> TYPE: DNA
<213> ORGANISM: Artificial Sequence
<220> FEATURE:
<223> OTHER INFORMATION: rDer f 2 primer

<400> SEQUENCE: 25
tcaaacaatg tttttgt                                                   18

<210> SEQ ID NO 26
<211> LENGTH: 18
<212> TYPE: DNA
<213> ORGANISM: Artificial Sequence
<220> FEATURE:
<223> OTHER INFORMATION: rDer f 10 primer

<400> SEQUENCE: 26
atggaggcca tcaagaaa                                                  18

<210> SEQ ID NO 27
<211> LENGTH: 20
<212> TYPE: DNA
<213> ORGANISM: Artificial Sequence
<220> FEATURE:
<223> OTHER INFORMATION: rDer f 10 primer

<400> SEQUENCE: 27
ctgtctgcgt aatatgaaag                                                20

<210> SEQ ID NO 28
<211> LENGTH: 21
<212> TYPE: DNA
<213> ORGANISM: Artificial Sequence
<220> FEATURE:
<223> OTHER INFORMATION: rDer f 11 primer

<400> SEQUENCE: 28
```

```
cacattgaat cggaagaaac g                                              21

<210> SEQ ID NO 29
<211> LENGTH: 21
<212> TYPE: DNA
<213> ORGANISM: Artificial Sequence
<220> FEATURE:
<223> OTHER INFORMATION: rDer f 11 primer

<400> SEQUENCE: 29
tgattctaat tccacttcca a                                              21

<210> SEQ ID NO 30
<211> LENGTH: 20
<212> TYPE: DNA
<213> ORGANISM: Artificial Sequence
<220> FEATURE:
<223> OTHER INFORMATION: rDer f 11 primer

<400> SEQUENCE: 30
atggcaagca ttgaaggtaa                                                20

<210> SEQ ID NO 31
<211> LENGTH: 20
<212> TYPE: DNA
<213> ORGANISM: Artificial Sequence
<220> FEATURE:
<223> OTHER INFORMATION: rDer f 11 primer

<400> SEQUENCE: 31
ttagattcgt ttatatgttc                                                20

<210> SEQ ID NO 32
<211> LENGTH: 20
<212> TYPE: DNA
<213> ORGANISM: Artificial Sequence
<220> FEATURE:
<223> OTHER INFORMATION: rDer f 13 primer

<400> SEQUENCE: 32
atggatccgt caacattgag                                                20

<210> SEQ ID NO 33
<211> LENGTH: 24
<212> TYPE: DNA
<213> ORGANISM: Artificial Sequence
<220> FEATURE:
<223> OTHER INFORMATION: rDer f 13 primer

<400> SEQUENCE: 33
tcagttgtct tcgacgatga aatt                                           24

<210> SEQ ID NO 34
<211> LENGTH: 20
<212> TYPE: DNA
<213> ORGANISM: Artificial Sequence
<220> FEATURE:
<223> OTHER INFORMATION: rDer f 14 primer

<400> SEQUENCE: 34
atggctgcta atcctgaatc                                                20

<210> SEQ ID NO 35
<211> LENGTH: 23
<212> TYPE: DNA
```

```
<213> ORGANISM: Artificial Sequence
<220> FEATURE:
<223> OTHER INFORMATION: rDer f 14 primer

<400> SEQUENCE: 35
ttacgatgaa tgcaatgtat gac                                          23

<210> SEQ ID NO 36
<211> LENGTH: 20
<212> TYPE: DNA
<213> ORGANISM: Artificial Sequence
<220> FEATURE:
<223> OTHER INFORMATION: rDer f 30 primer

<400> SEQUENCE: 36
atgtctacta caaattattc                                              20

<210> SEQ ID NO 37
<211> LENGTH: 23
<212> TYPE: DNA
<213> ORGANISM: Artificial Sequence
<220> FEATURE:
<223> OTHER INFORMATION: rDer f 30 primer

<400> SEQUENCE: 37
ttagatcaat ttaacatgat gcc                                          23

<210> SEQ ID NO 38
<211> LENGTH: 21
<212> TYPE: DNA
<213> ORGANISM: Artificial Sequence
<220> FEATURE:
<223> OTHER INFORMATION: rDer f 32 primer

<400> SEQUENCE: 38
atggcccaag tggaagtaaa a                                            21

<210> SEQ ID NO 39
<211> LENGTH: 25
<212> TYPE: DNA
<213> ORGANISM: Artificial Sequence
<220> FEATURE:
<223> OTHER INFORMATION: rDer f 32 primer

<400> SEQUENCE: 39
ctaatttaaa ttcgaatttt tattc                                        25

<210> SEQ ID NO 40
<211> LENGTH: 26
<212> TYPE: DNA
<213> ORGANISM: Artificial Sequence
<220> FEATURE:
<223> OTHER INFORMATION: rDer f Alt a 10 primer

<400> SEQUENCE: 40
atggcccaag tggaagtaaa atatac                                       26
```

```
<210> SEQ ID NO 41
<211> LENGTH: 25
<212> TYPE: DNA
<213> ORGANISM: Artificial Sequence
<220> FEATURE:
<223> OTHER INFORMATION: rDer f Alt a 10 primer

<400> SEQUENCE: 41
ctaatttaaa ttcgaatttt tattc                                              25
```

COMPOSITION FOR DIAGNOSING ALLERGIES TO MITES, METHOD OF DIAGNOSING ALLERGIES TO MITES, AND COMPOSITION FOR PREVENTING OR TREATING ALLERGIES TO MITES

CROSS-REFERENCE TO RELATED APPLICATION

This application is a division of U.S. patent application Ser. No. 16/138,357, filed on Sep. 21, 2018, which claims the benefit of Korean Patent Application No. 10-2017-0122870, filed on Sep. 22, 2017, in the Korean Intellectual Property Office, the disclosures of which are incorporated herein in their entirety by reference.

REFERENCE TO A SEQUENCE LISTING

This application incorporates by reference the Sequence Listing submitted in Computer Readable Form as file 262850_US_Sequence_Listing.txt, created on May 3, 2021 and containing 52,508 bytes.

BACKGROUND

1. Field

The present disclosure relates to a composition and a kit for diagnosing allergies to mites, a method of diagnosing allergies to mites, and a composition for preventing or treating allergies to mites.

2. DESCRIPTION OF THE RELATED ART

House dust mites (HDM) are the most ubiquitous indoor aeroallergen worldwide.

Sensitization due to chronic and continuous exposure to allergens causes a variety of diseases throughout one's lifetime, starting from a young age. Sensitization to HDM may cause allergic rhinitis (AR), allergic asthma (AA), and atopic dermatitis (AD).

Major species of pathogenic mites causing allergic diseases include *Dermatophagoides farinae* (*D. farinae*) and *Dermatophagoides pteronyssinus* (*D. pteronyssinus*). These two species account for about 90% of HDM allergies. Sensitization profiles of HDM show geographical variations. D. farina is predominant in dry regions, while *D. pteronyssinus* lives in humid regions. In Korea, most of the patients sensitized to storage mites are also sensitized to HDM, and thus they tend to show cross-reactivity.

Recently, it has been reported that various components of HDM, for example, mite body, feces, eggs, exuviae, etc., are associated with various allergic diseases, and the respective proteins having various immunological-biological characteristics. For this reason, HDM may cause various diseases during the development of allergies, and HDM may cause various sensitization patterns. Precise identification of sensitization patterns is important for accurate diagnosis and treatment, particularly for allergen specific immunotherapy (AIT).

Accordingly, the present inventors analyzed IgE reactivities in Korean patients with HDM allergies who showed various clinical signs, and they identified allergens specific to allergic diseases, thereby completing the present disclosure.

SUMMARY

An aspect provides a composition for diagnosing an allergic disease to at least one mite species.

Another aspect provides a kit for diagnosing an allergic disease to at least one mite species.

Still another aspect provides a method of providing information which is needed to diagnose an allergic disease to at least one mite species.

Still another aspect provides a composition for preventing or treating an allergic disease to at least one mite species.

BRIEF DESCRIPTION OF THE DRAWINGS

These and/or other aspects will become apparent and more readily appreciated from the following description of the embodiments, taken in conjunction with the accompanying drawings in which:

FIGS. 1A to 1D show differences in IgE reactivities between allergic respiratory disease patients and atopic dermatitis patients, in which FIG. 1A shows a protein profile of *Dermatophagoides farinae*, FIG. 1B shows IgE reactivity of allergic respiratory disease patients, FIG. 1C shows IgE reactivity of atopic dermatitis-accompanying allergic respiratory disease patients, and FIG. 1D shows IgE reactivity of atopic dermatitis patients;

FIGS. 2A to 2D show differences in IgE reactivities between allergic respiratory disease patients and allergic dermatitis patients, as analyzed by two-dimensional protein separation, in which FIG. 2A shows a protein profile of *Dermatophagoides farinae*, FIG. 2B shows IgE reactivity of allergic respiratory disease patients, FIG. 2C shows IgE reactivity of atopic dermatitis-accompanying allergic respiratory disease patients, and FIG. 2D shows IgE reactivity of atopic dermatitis patients;

DETAILED DESCRIPTION

Figure 1A:
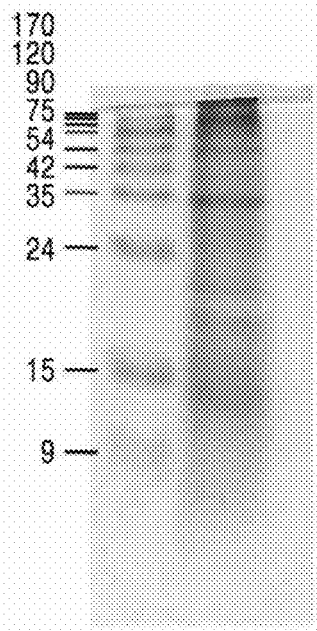
Figure 1B:
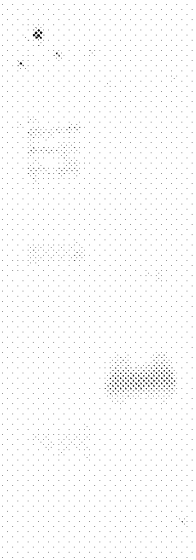
Figure 1C:
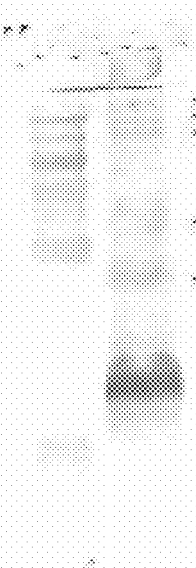
Figure 1D:
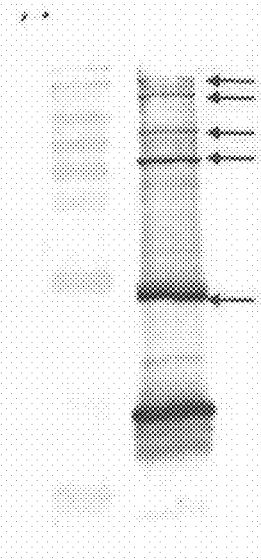
Figure 2A:
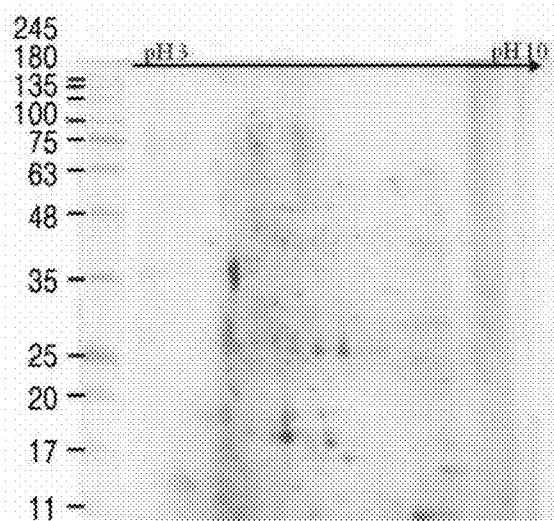
Figure 2B:
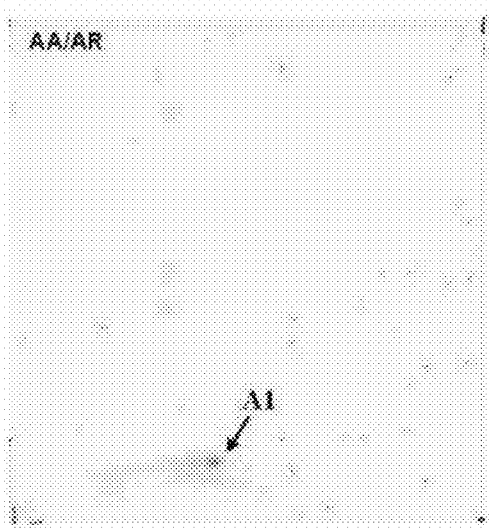
Figure 2C:
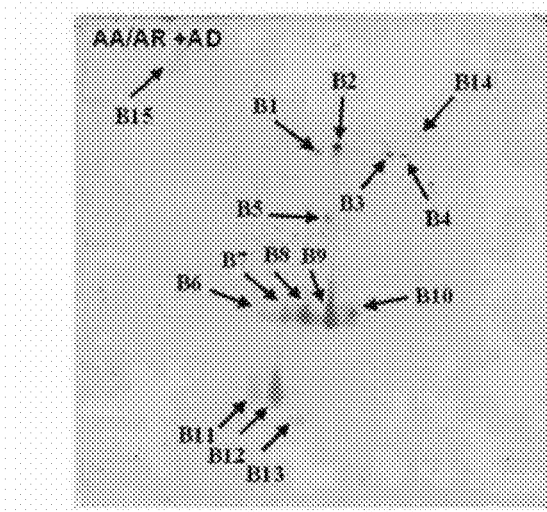
Figure 2D:
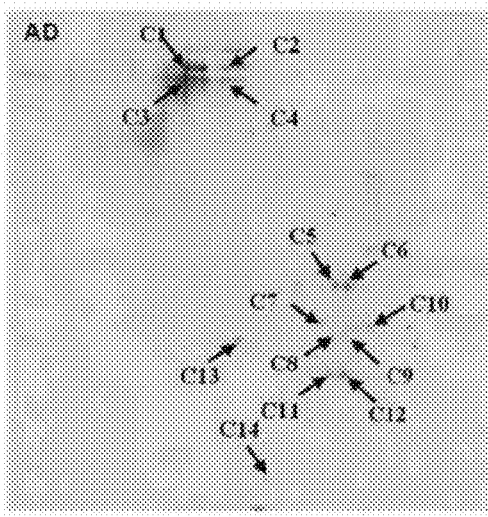

An aspect provides a composition for diagnosing allergies to mites, the composition including Der f 11, Der f 13, Der f 14, Der f 32, Der f Alt a 10, or a combination thereof. The protein may include a polypeptide or a fragment thereof, wherein the polypeptide may include an amino acid sequence having about 95% or more, about 96% or more, about 97% or more, about 98% or more, about 99% or more, or 100% sequence homology with any one amino acid sequence selected from SEQ ID NOS: 1, 3, 5, 7, and 9. The composition may include a polypeptide or a fragment thereof, or a combination thereof, wherein the polypeptide may include an amino acid sequence having about 95% or more, about 96% or more, about 97% or more, about 98% or more, about 99% or more, or 100% sequence homology with any one amino acid sequence selected from SEQ ID NOS: 1, 3, 5, 7, and 9.

Der f 11 is a fragment of paramyosin and has about 98 kDa. Der f 11 may include an amino acid sequence registered as GenBank Accession number AAK39511.1, European Nucleotide Archive number A1008864, or UniProtKB Accession number Q967Z0, or an amino acid sequence of SEQ ID NO: 1 or SEQ ID NO: 19, or an amino acid sequence which is encoded by a nucleotide sequence registered as GenBank Accession number AF352244, or a nucleotide sequence of SEQ ID NO: 2. Der f 13 is a fatty acid-binding protein and has about 15 kDa. Der f 13 may include an amino acid sequence registered as GenBank Accession number AAP35078, European Nucleotide Archive number AAP35078.1, or UniProtKB Accession Number Q1M2P5, or an amino acid sequence of SEQ ID NO: 3, or an amino acid sequence which is encoded by a nucleotide sequence registered as GenBank Accession number AY283293, or a nucleotide sequence of SEQ ID NO: 4. Der f 14 is a fragment of apolipophorin and has about 177 kDa. Der f 14 may include an amino acid sequence registered as GenBank Accession number BAA04558, European Nucleotide Archive number P39673, or UniProtKB Accession Number Q94507, or an amino acid sequence of SEQ ID NO: 5 or SEQ ID NO: 20, or an amino acid sequence which is encoded by a nucleotide sequence registered as GenBank Accession number D17686, or a nucleotide sequence of SEQ ID NO: 6. Der f 32 is secreted inorganic pyrophosphatase and has about 35 kDa. Der f 32 may include an amino acid sequence registered as GenBank Accession number A1008849.1, or European Nucleotide Archive number A1008849, or an amino acid sequence of SEQ ID NO: 7, or an amino acid sequence which is encoded by a nucleotide sequence registered as GenBank Accession number KM009993, or a nucleotide sequence of SEQ ID NO: 8. Der f Alt a 10 is aldehyde dehydrogenase and has about 53 kDa. Der f Alt a 10 may include an amino acid sequence registered as UniProtKB Accession Number A1KXH7 or European Nucleotide Archive number AAP35081, or an amino acid sequence of SEQ ID NO: 9, or an amino acid sequence which is encoded by a nucleotide sequence registered as European Nucleotide Archive number AY283296, or a nucleotide sequence of SEQ ID NO: 10.

The composition may include Der f 1, Der f 2, Der f 10, Der f 30, or a combination thereof. The protein may include a polypeptide or a fragment thereof, wherein the polypeptide may include an amino acid sequence having about 95% or more, about 96% or more, about 97% or more, about 98% or more, about 99% or more, or 100% sequence homology with any one amino acid sequence selected from SEQ ID NOS: 11, 13, 15, and 17. The composition may include a polypeptide or a fragment thereof, or a combination thereof, wherein the polypeptide may include an amino acid sequence having about 95% or more, about 96% or more, about 97% or more, about 98% or more, about 99% or more, or 100% sequence homology with any one amino acid sequence selected from SEQ ID NOS: 11, 13, 15, and 17.

Der f 1 is cysteine protease and has 27 kDa. Der f 1 may include an amino acid sequence registered as GenBank Accession number BAC53948, or UniProtKB Accession Number Q58A71, or an amino acid sequence of SEQ ID NO: 11 or SEQ ID NO: 21, or an amino acid sequence which is encoded by a nucleotide sequence registered as GenBank Accession number AB034946 or a nucleotide sequence of SEQ ID NO: 12 or SEQ ID NO: 22. Der f 2 is an NPC2 family and has 15 kDa. Der f 2 may include an amino acid sequence registered as GenBank Accession number BAA01240 or UniProtKB Accession Number Q00855, or an amino acid sequence of SEQ ID NO: 13, or an amino acid sequence which is encoded by a nucleotide sequence registered as GenBank Accession number D10448 or a nucleotide sequence of SEQ ID NO: 14. Der f 10 is tropomyosin and has 37 kDa. Der f 10 may include an amino acid sequence registered as GenBank Accession number BAA04557 or UniProtKB Accession Number Q23939, or an amino acid sequence of SEQ ID NO: 15, or an amino acid sequence which is encoded by a nucleotide sequence registered as GenBank Accession number D17682 or a nucleotide sequence of SEQ ID NO: 16. Der f 30 is ferritin and has 16 kDa. Der f 30 may include an amino acid sequence registered as GenBank Accession number GC56219.1 or UniProtKB Accession Number L7UZ91, or an amino acid sequence of SEQ ID NO: 17, or an amino acid sequence which is encoded by a nucleotide sequence registered as GenBank Accession number KC305503 or a nucleotide sequence of SEQ ID NO: 18.

The "homology" means a percentage of identity between nucleotide sequences of two polynucleotides or between amino acid sequences of two polypeptides. A sequence homology between one moiety and another moiety may be determined by technologies known in the art, and for example, determined by a BLAST algorithm as disclosed in a literature [see Karlin and Altschul, Pro. Natl. Acad. Sci. USA, 90, 5873(1993)] or by Pearson's FASTA [see Methods Enzymol., 183, 63(1990)].

The "fragment" means a part of a polypeptide, not the whole polypeptide, and reacts with IgE antibody to induce an antigen-antibody reaction. The protein may be, derived from a mite, an allergen causing an allergic disease. The protein may be a mite body, feces, egg, or exuviae, or a combination thereof.

The protein may be recombinantly prepared using animal cells or bacteria. The protein may include an additional amino acid sequence. The protein may include, for example, an additional amino acid sequence at the N-terminus and/or C-terminus of a polypeptide having an amino acid sequence of SEQ ID NO: 1 or a fragment thereof. The additional amino acid sequence may be added in order to purify the recombinantly prepared protein, for example, in order to apply the protein to affinity column chromatography. The bacteria may be microorganisms of the genus *Escherichia*, and for example, *E. coli*. The bacteria may be *Pichia*. With regard to the composition, when the protein is recombinantly prepared and expressed in bacteria, the protein may be obtained by introducing into the bacteria a polynucleotide having a nucleotide sequence encoding a polypeptide or a fragment thereof, wherein the polypeptide includes an amino acid sequence having about 95% or more sequence homology with the amino acid sequence of the above SEQ ID NO. The polynucleotide having the nucleotide sequence may be codon-optimized for the bacteria.

Introduction of the polynucleotide into bacteria may be, for example, introduction of the polynucleotide in the form of an expression cassette or introduction of the polynucleotide itself. The expression cassette may include all elements required for autonomous expression of the polynucleotide. The expression cassette may include a promoter operably linked to the polynucleotide, a transcription termination signal, a ribosome binding site, and a translation termination signal. The expression cassette may be in the form of a self-replicable expression vector. The vector may be an expression vector known in the art. For introduction of the polynucleotide itself, the polynucleotide may be operably linked to a sequence needed for expression in a host cell to be introduced. The bacteria into which the polynucleotide is introduced may be transformed bacteria.

Culturing of the bacteria for the production of the recombinant protein may be performed according to appropriate media and culture conditions known in the art. Those skilled in the art may easily modify the culture process depending on a selected strain. The culture method may include batch culture, continuous culture, and fed-batch culture, but is not limited thereto. Various methods of culturing microorganisms are disclosed in, for example, Biochemical Engineering, James M. Lee, Prentice-Hall International Editions.

The media may include a variety of carbon sources, nitrogen sources, and trace elements. Carbon sources that are applicable to media for culturing microorganisms may include carbohydrates such as glucose, sucrose, lactose, fructose, maltose, starch, and cellulose; oils such as soybean oil, sunflower oil, castor oil, and coconut oil; fatty acids such as palmitic acid, stearic acid, and linoleic acid; alcohols such as glycerol and ethanol; and organic acids such as acetic acid, but are not limited thereto. These carbon sources may be used alone or in combination thereof. Nitrogen sources that are applicable to media for culturing microorganisms may include organic nitrogen sources such as peptone, yeast extract, meat extract, malt extract, corn steep liquor, and soybean meal, and inorganic nitrogen sources such as urea, ammonium sulfate, ammonium chloride, ammonium phosphate, ammonium carbonate and ammonium nitrate, but are not limited thereto. These nitrogen sources may be used alone or in combination thereof. Phosphorus sources that are applicable to media for culturing microorganisms may include potassium phosphate monobasic, potassium phosphate dibasic, and corresponding sodium-containing salts. The media may further include a metal salt such as magnesium sulfate or iron sulfate. In addition, the media may include amino acids, vitamins, appropriate precursors, etc. The media for culturing microorganisms or individual components may be added to culture media in a batch or continuous manner.

The "allergen" means an antigen that causes an allergic disease or an antigen that is a cause of an allergic disease. Once antibodies are produced in a human body by intake or contact of any kind of a substance containing the allergen, an antigen-antibody reaction may occur by re-intake or re-contact of the same substance.

With regard to the composition, since the protein is an allergen which is a cause of allergies to mites, allergies to mites may be diagnosed by examining an antigen-antibody reaction between the protein and IgE antibodies in a biological sample isolated from a subject.

The "diagnosis" means confirming the presence or characteristics of pathological state. Therefore, the diagnosis of allergies to mites means confirming or predicting occurrence of allergies to mites or possibility of occurrence of allergies to mites.

The "antibody" is, a term known in the art, a specific polypeptide directed against an antigenic region, or a fragment thereof. The IgE antibody is a sensitizing antibody produced by an allergen, and produced by plasma cells, and binds to a receptor on the surface of mast cells or basophils. IgE antibody may cause anaphylaxis (a specific symptom caused by an antigen-antibody reaction).

The mite may be a house dust mite, a storage mite, or a combination thereof. The mite may be *Dermatophagoides farina*, *Dermatophagoides pteronyssinus*, Euroglyphus *maynei*, Tyrophagus putrescentiae, *Blomia tropicalis*, or a combination thereof. That is, since there is cross-reactivity between mites, the allergic disease may be caused by *Dermatophagoides farinae*, *Dermatophagoides pteronyssinus*, Euroglyphus *maynei*, Tyrophagus putrescentiae, *Blomia tropicalis*, or a combination thereof.

The allergic disease may be targeted to a people including Korean. The allergic disease may be allergic asthma, allergic rhinitis, atopic dermatitis, or a combination thereof. When a positive reaction is detected in the binding between IgE antibody in a sample and Der f 1, Der f 2, or a combination thereof, the sample may be diagnosed with allergic disease. When a positive reaction is detected in the binding between IgE antibody in a sample and Der f 11, Der f 13, Der f 14, Der f 32, Der f Alt a 10, or a combination thereof, the sample may be diagnosed with allergic dermatitis. When a negative reaction is detected in the binding between IgE antibody in a sample and Der f 11, Der f 13, Der f 14, Der f 32, Der f Alt a 10, or a combination thereof, the sample may be diagnosed with allergic respiratory disease.

Clinical symptoms of a patient may be accurately predicted and appropriate immunotherapy may be applied to the patient by monitoring allergen sensitization patterns and profiles during progression of allergic reaction.

Another aspect provides a kit for diagnosing allergies to mites, the kit including Der f 11, Der f 13, Der f 14, Der f 32, Der f Alt a 10, or a combination thereof.

The kit may include Der f 1, Der f 2, Der f 10, Der f 30, or a combination thereof.

The protein, polypeptide or fragment thereof, composition, mite, diagnosis of allergies are the same as described above.

The kit may be manufactured into many different kinds of known kits. For example, the kit may be a kit for immunoassay, which may qualitatively or quantitatively analyze reactivity between the protein and IgE antibodies in a biological sample isolated from a subject.

The kit may include a solid substrate which is coated with the protein, anti-IgE antibody which is able to bind to IgE antibodies in a biological sample isolated from a subject and is conjugated with a label generating a detectable signal, and a reagent which is needed to detect an antigen (allergen)-antibody (IgE) reaction. The solid substrate may be hydrocarbon polymers (e.g., polystyrene, polypropylene, etc.), glass, metals, or gels. The solid substrate may be a microtiter plate. The label generating a detectable signal may include a chemical (e.g., biotin, etc.), an enzyme (e.g., alkaline phosphatase, β-galactosidase, horseradish peroxidase, Cytochrome P450, etc.), a radioactive substance, a fluorescent substance (e.g., fluorescein, etc.), a luminescent substance, a chemiluminescent substance, and fluorescence resonance energy transfer (FRET), but is not limited thereto. Various labels and labeling methods are described in Ed Harlow and David Lane, Using Antibodies:A Laboratory Manual, Cold Spring Harbor Laboratory Press, 1999. The kit may be manufactured to have a plurality of separate packages or compartments including the above-described components.

Still another aspect provides a method of detecting binding of Der f 11, Der f 13, Der f 14, Der f 32, Der f Alt a 10, or a combination thereof and IgE antibodies in a biological sample isolated from a subject, in order to provide information needed for diagnosis of allergies to mites.

The method may include detecting binding of Der f 1, Der f 2, Der f 10, Der f 30, or a combination thereof and IgE antibodies in a biological sample isolated from a subject.

The protein, polypeptide or fragment thereof, composition, mite, and diagnosis of allergies are the same as described above.

The "subject" means a subject who is examined or predicted in order to confirm whether or not having an allergic disease to at least one mite species or having possibility of an allergic disease to at least one mite species. The subject may be a vertebrate, specifically a mammal, an amphibian, a reptile, a bird, etc., and more specifically a mammal, for example, a human (Homo sapiens). The human may be a Korean people.

The "biological sample" may include tissues, cells, whole blood, serum, plasma, saliva, sputum, cerebrospinal fluid, urine, etc., which is separated from the subject, but is not limited thereto.

The method may be performed by immunoassay (antigen-antibody reaction). The immunoassay may include radioimmunoassay, radioimmuno-precipitation, immuno-precipitation, enzyme-linked immunosorbent assay (ELISA), capture-ELISA, inhibition or competition assay, sandwich assay, flow cytometry, immunofluorescence staining, and immunoaffinity purification, but is not limited thereto. The immunoassay is described in Enzyme Immunoassay, E. T. Maggio, ed., CRC Press, Boca Raton, Fla., 1980; Gaastra, W., Enzyme-linked immunosorbent assay (ELISA), in Methods in Molecular Biology, Vol. 1, Walker, J. M. ed., Humana Press, N J, 1984; and Ed Harlow and David Lane, Using Antibodies:A Laboratory Manual, Cold Spring Harbor Laboratory Press, 1999, which may be served as a reference.

For example, when the method is performed by the radioimmunoassay method, an antibody (IgE-specific antibody) labeled with a radioisotope (e.g., $C^{14}$, $I^{125}$, $P^{32}$, $S^{35}$, etc.) may be used. In the method, antibody bound with the above-described label generating a detectable signal may be also used. For example, when the method is performed by the ELISA method, the method may include (i) coating a surface of a solid substrate with the identified protein; (ii) adding a biological sample isolated from a subject to the coated solid substrate; (iii) reacting the resultant of (ii) with an anti-IgE secondary antibody conjugated with an enzyme; and (iv) measuring activity of the enzyme. The enzyme conjugated to the secondary antibody may include an enzyme catalyzing colorimetric, fluorometric, luminescence, or infra-red reactions, but is not limited thereto, and for example, alkaline phosphatase, β-galactosidase, horseradish peroxidase, luciferase, or Cytochrome P450. When alkaline phosphatase is used as the enzyme conjugated to the secondary antibody, a colorimetric substrate such as bromochloroindolyl phosphate, nitro blue tetrazolium, naphthol-AS-B1-phosphate, or enhanced chemifluorescence (ECF) may be used as a substrate. When horseradish peroxidase is used, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), p-phenylenediamine-HCl and pyrocatechol (HYR), tetramethylbenzidine (TMB), 2,2'-azine-di[3-ethylbenzthiazoline sulfonate (ABTS), o-phenylenediamine, naphthol/pyronine, glucose oxidase and t-nitroblue tetrazolium (t-NBT) or m-phenazine methosulfate (m-PMS) may be used as a substrate.

Providing information needed for diagnosis of allergies to mites may be for prediction or diagnosis of relative risk of allergies to mites. When a positive reaction is detected in biding between IgE antibody and Der f 1, Der f 2, or a combination thereof, it may be determined that the subject belongs to a high risk group for the development of allergies to mites. When a positive reaction is detected in biding between IgE antibody and Der f 11, Der f 13, Der f 14, Der f 32, Der f Alt a 10, or a combination thereof, it may be determined that the subject belongs to a high risk group for the development of atopic dermatitis to mites. When a negative reaction is detected in biding between IgE antibody and Der f 11, Der f 13, Der f 14, Der f 32, Der f Alt a 10, or a combination thereof, it may be determined that the subject belongs to a high risk group for the development of allergic respiratory diseases to mites.

In the method, measurement of the final enzymatic activity or measurement of the signal may be performed according to various methods known in the art. The detection of the signal indicates binding of the protein and IgE in the biological sample isolated from the subject, and this information may be utilized in diagnosing allergies to mites.

Still another aspect provides a composition for preventing or treating allergies to mites, the composition including Der f 11, Der f 13, Der f 14, Der f 32, Der f Alt a 10, or a combination thereof.

The composition may include Der f 1, Der f 2, Der f 10, Der f 30, or a combination thereof.

The composition may be an immunotherapy composition for preventing or treating allergies to mites.

The "immunotherapy (allergen immunotherapy)" means a therapy of reducing sensitivity or hypersensitivity to a specific allergen by administering an allergen which is a cause of allergic disease to the subject via injection, starting with a low dose, with gradual increases in dose for a predetermined period. That is, the immunotherapy means a hyposensitization therapy for a causative allergen. The immunotherapy may be performed via subcutaneous injection and/or respiratory tract. Such an immunotherapy may be a therapy consisting of two phases: an initial therapy of reaching a maintenance dose by gradually increasing a dose of allergen, starting from a low dose, and a maintenance therapy of maintaining the dose for 3 years to 5 years; a therapy of administering a high dose of allergen for a day to a week immediately before the season; or a therapy of administering a low dose of allergen for several years. Through the immunotherapy of administering the protein or the composition, manifestation of symptoms by antigen-antibody reactions may be prevented or inhibited at the time of subsequent exposure to the allergen. In other words, since the protein is a cause of allergies to mites, the protein may be used in the immunotherapy for preventing or treating allergies to mites.

The composition may be a pharmaceutical composition. The pharmaceutical composition may include the allergen which is the active ingredient in an amount of about 0.0001% by weight to about 50% by weight, with respect to the total weight of the composition. For administration, the pharmaceutical composition may be prepared by further including one or more pharmaceutically acceptable carriers, in addition to the above-described active ingredient. The pharmaceutically acceptable carrier may include a saline solution, sterilized water, Ringer's solution, buffered saline, a dextrose solution, a maltodextrin solution, glycerol, ethanol, liposome, and a mixture of one or more thereof. As needed, other common additives such as an antioxidant, a buffer solution, a bacteriostatic agent, etc. may be added. Further, the composition may be formulated into injectable formulations such as aqueous solutions, suspensions, emulsions, etc., pills, capsules, granules, or tablets by additionally adding a diluent, a dispersant, a surfactant, a binder, and a lubricant. It is also possible to bind such carriers with a target organ-specific antibody or other ligands so that they may act specifically on a target organ. Furthermore, the composition may be formulated depending on diseases or ingredients according to an appropriate method known in the art or a method described in a literature (Remington's Pharmaceutical Science, Mack Publishing Company, Easton Pa.).

The pharmaceutical composition may be formulated for oral, topical, parenteral, intranasal, intravenous, intramuscular, subcutaneous, intraocular, or transdermal administration. The pharmaceutical composition may be administered orally or parenterally at the time of clinical administration. Upon parenteral administration, the pharmaceutical composition may be administered intranasally, sublingually, or intratracheally, or by intraperitoneal, intrarectal, subcutaneous, intravenous, intramuscular, intracerebrovascular, or intrathoracic injection. The administration subject may be a mammal such as a human, a pig, a cow, a horse, a dog, a cat, or an experimental animal, e.g., a mouse, a rat, a rabbit, a guinea pig, or a hamster. An administration dosage of the composition to be used may be controlled by various parameters, in particular, the mode of administration or duration of treatment. In addition, a range thereof may be controlled depending on the subject's body weight, age, sex, health status, diet, excretion rate, and severity of allergy symptoms to mites. A daily dose may be about 0.0001 mg/kg to about 100 mg/kg, or about 0.001 mg/kg to about 10 mg/kg once or several times a day. By identifying sensitization profiles between respiratory diseases and skin diseases induced by mites, more accurate diagnosis and immunotherapy are possible.

The mite proteins according to an aspect may be used in diagnosing allergic diseases. Results of diagnosing allergic diseases by using the proteins have high reliability and validity. Further, the proteins may be used in a composition for preventing or treating allergic diseases.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein.

Accordingly, the embodiments are merely described below, by referring to the figures, to explain aspects of the present description. As used herein, the term "and/or" includes any and all combinations of one or more of the associated listed items.

Hereinafter, the present disclosure will be described in more detail with reference to Examples. However, these Examples are for illustrative purposes only, and the present disclosure is not intended to be limited by these Examples.

Example 1. Identification of Pathogenesis-Related Protein Molecules in Mites and Analysis of Reactivities Thereof in Allergic Disease Patients 1. Selection of Patients and Statistical Analysis in Allergic Rhinitis, Allergic Asthma, or Atopic Dermatitis Patients This study was approved by the Institutional Review Board of Yonsei University Health System (4-2013-0397), and conducted in the Allergy and Asthma Clinic of Severance Hospital. Selection criteria for HDM allergy patients are as follows: 1) patients aged 6 to 80 years, 2) patients (AA, AR, or AD) who were diagnosed with HDM allergic disease by allergists, and 3) HDM sensitization confirmed by skin prick test (SPT) for *D. farinae* or specific IgE (sIgE) detection. Patients under ATI treatment were excluded. Subsequently, the patients were divided into three groups: 1) patients only with allergic respiratory disease, 2) patients with both allergic respiratory disease and atopic dermatitis, and 3) patients only with atopic dermatitis. 20 persons were selected as controls. All participants signed a written consent form. Blood samples were collected from all the subjects, and stored at about −70° C. for further experiments.

Statistical data of 160 HDM allergy patients are shown in Table 1 below. In the following Table 1, age and wheal size are presented as the mean±standard deviation. The mean age of the patients was about 26.7 years. Of the three groups classified by clinical diagnosis, the atopic dermatitis patient group was younger (P<0.001) and showed higher sIgE titers than the allergic respiratory disease patient group. Allergic conjunctivitis, food allergy, and drug allergy were common in the allergic respiratory disease patient group, as compared with the atopic dermatitis patient group. The atopic dermatitis patient group showed the highest value in total IgE titer (p<0.001). There was no difference in the size of wheal to *D. farinae* between groups. However, the atopic dermatitis patient group showed the highest value in sIgE titer of *D. farinae* (p<0.001).

TABLE 1

|  | Total (n = 160) | AA/AR (n = 67) | AA/AR + AD (n = 41) | AD (n = 52) | P value |
| --- | --- | --- | --- | --- | --- |
| Age (year) | 26.7 ± 15.7 | 33.6 ± 17.9 | 21.1 ± 10.9 | 22.2 ± 12.4 | <0.001 |
| Male:Female | 97:63 | 38:29 | 27:14 | 32:20 | 0.573 |
| Diagnosis, n(%) |  |  |  |  |  |
| Allergic asthma (AA) | 68(42.5) | 49(72.1) | 19(46.3) | 0(0) | <0.001 |
| Allergic rhinitis (AR) | 102(63.8) | 65(97.0) | 37(90.2) | 0(0) | <0.001 |
| Atopic dermatitis (AD) | 93(58.1) | 0(0) | 41(100) | 52(100) | <0.001 |
| Allergic conjunctivitis | 33(20.6) | 17(25.4) | 14(34.1) | 2(3.8) | 0.001 |
| Food allergy | 18(11.3) | 14(20.9) | 1(2.4) | 3(5.8) | 0.002 |
| Drug allergy | 4(2.5) | 4(6.0) | 0(0) | 0(0) | 0.031 |
| Total IgE (kU/L) | 1513.7 ± 1637.4 | 547.9 ± 585.1 | 1910.8 ± 1859.2 | 2146.9 ± 1747.4 | <0.001 |
| *D. farinae* sensitization |  |  |  |  |  |
| Wheal size(mm) | 8.4 ± 5.7 | 8.5 ± 6.0 | 8.0 ± 5.5 | 8.2 ± 3.8 | 0.875 |
| sIgE titer (kU$_A$/L) | 53.6 ± 41.1 | 31.8 ± 29.9 | 64.3 ± 43.1 | 73.2 ± 39.2 | <0.001 |

2. Skin Prick Test (SPT) of Allergic Disease Patients 53 kinds of aeroallergens (HDM, tree pollen, grass pollen, weed pollen, mold, dander, and cockroach) were used to perform a skin prick test. A saline solution containing 0.3% phenol and 50% glycerol was used as a negative control, and a saline solution containing 0.1% histamine (Allergy Therapeutics, Worthing, UK) was used as a positive control. Administration of drugs which may influence SPT was stopped for all patients. 15 minutes after allergen administration, results of SPT were analyzed. A wheal larger than 3 mm was determined as a positive reaction.

3. Analysis of Characteristics and IgE Reactivity of *D. farinae* (I)

Standardized *D. farinae* extract (20 pg, Yonsei Allergy Institute, Seoul, Korea) was separated by sodium dodecyl sulfate polyacrylamide gel electrophoresis (SDS-PAGE) using a 15% gel. Subsequently, separated proteins were transferred to polyvinylidene difluoride (PVDF) membranes (0.45 µm, GE Water & Process Technologies, Trevose, Pa., USA). The membranes were incubated in 3% skim milk overnight to block non-specific binding. Then, sera of patients were added thereto, followed by incubation at 37° C. overnight. Next, 1:1000-diluted mouse anti-human IgE (Southern Biotech, Birmingham, Ala.) was added and incubated for 1 hour. Next, nitro blue tetrazolium and 5-bromo-4-chloro-3-indolyl-phosphate (Promega, Madison, Wis.) were used for color development.

Differences in IgE reactivity between allergic respiratory disease patient and atopic dermatitis patient are shown in FIG. 1. FIG. 1A is an image showing separation of proteins of *D. farinae* under denaturation conditions. FIG. 1B shows IgE reactivities of sera collected from the subjects with respiratory allergy. Referring to FIG. 1B, a clear single band of 14 kDa was detected. Referring to FIGS. 1C and 1D, the atopic dermatitis patient group showed multiple IgE reactivities to mite proteins having different sizes, as compared with the allergic respiratory disease patient group.

4. Analysis of Characteristics and IgE Reactivity of *D. farinae* (II)

Mite extract was desalted using trichloroacetic acid, and two-dimensional gel electrophoresis was performed. 0.1 mg of HDM extract was subjected to electrophoresis on an isoelectric focusing gel of pH 3 to pH 10, and separated on a 15% sodium dodecyl sulfate polyacrylamide gel. The separated proteins were stained with Coomassie blue or transferred to a PVDF membrane (Millipore, Billerica, USA), followed by immunoblotting. Thereafter, IgE reactive components were examined in pooled sera of 10 subjects (1: 4). IgE antibody was detected by alkaline phosphatase-conjugated goat anti-human IgE (1:1000) (Sigma-Aldrich). Next, nitro blue tetrazolium and 5-bromo-4-chloro-3-indolyl-phosphate were used for color development. In order to identify IgE antibody-reactive proteins, LC-equipped ESI-MS/MS was performed in ProteomeTech (Seoul, Korea). Amino acid sequences of HDM-related proteins identified by this analysis were used to produce HDM CRD allergens.

In order to examine validity of the proteins detected in SDS-PAGE, two-dimensional electrophoresis and Western blotting were performed, and shown in FIG. 2. FIG. 2A shows results of separating proteins of *D. farinae* under denaturation conditions. Results of identifying proteins which specifically reacted with IgE antibody in each patient group are shown in FIGS. 2B to 2D. As shown in FIG. 2B, clear spots of 14 kDa were detected in the allergic asthma or allergic rhinitis patient group. Referring to FIGS. 2C and 2D, the atopic dermatitis patient group tended to react various HDM proteins, as compared with the allergic respiratory disease patient group. The spots indicated by arrows were analyzed by LC-equipped ESI-MS/MS. A1 spot in the allergic asthma or allergic rhinitis patient group was identified as Der f 2. 10 to 13 kinds of different allergens were identified in the atopic dermatitis patient group. 14 kinds of spots were detected in the atopic dermatitis-accompanying allergic asthma or allergic rhinitis patient group (B1 to B14 spots of FIG. 2). 13 kinds of spots were detected in the atopic dermatitis patient group (C1 to C13 spots of FIG. 2). HDM-related CRD allergens among 28 kinds of spots are as follows: Der f 1, Der f 2, Der f 11, Der f 13, Der f 14, Der f 30, and Der f Alt a 10. Results of identifying spots in two-dimensional electrophoresis are shown in Table 2 below.

TABLE 2

| point | Identification (origin) | Weight | Score |
|---|---|---|---|
| A1 | Der f 2 | 14,026 | 333 |
|  | Der f 13 | 14,971 | 103 |
| B1 | Nesprin-1(*Cerapachys biroi*) | 129,899 | 66 |
| B2 | Der f 1 | 23,763 | 100 |
| B4 | Nesprin-1(*Cerapachys biroi*) | 129,899 | 59 |
| B6 | Der f 1 | 23,763 | 209 |
|  | Der f 32 | 33,951 | 70 |
| B7 | Der f 1 | 23,763 | 145 |
| B8 | Der f 1 | 23,763 | 208 |
| B9 | Der f 1 | 23,763 | 179 |
| B10 | Der f Alt a 10 allergen | 54,162 | 83 |
| B11 | Der f 30 | 19,770 | 169 |
| B12 | Der f 30 | 19,770 | 248 |
| B13 | Der f 30 | 19,770 | 137 |
| B14 | AGAP009853-PA-like protein (*Anopheles sinensis*) | 46,460 | 58 |
| C1 | Der p 14 | 190,542 | 97 |
| C2 | Der f 11 | 102,407 | 510 |
| C3 | Mag 3 allergen | 40,520 | 79 |
| C4 | Der f 11 | 102,407 | 1,055 |
| C6 | Der f 14 | 39,643 | 295 |
| C9 | Alpha-enolase | 47,214 | 62 |
| C10 | Not detected |  |  |
| C11 | Der f 14 | 39,643 | 65 |
| C12 | Der f 14 | 39,643 | 93 |
| C13 | Cytochrome P450 3A9 (*Crassostrea gigas*) | 101,332 | 60 |

5. Preparation of HDM Component Allergens

Based on amino acid sequences of the analyzed allergens, recombinant allergens were prepared as follows.

Figure 3:
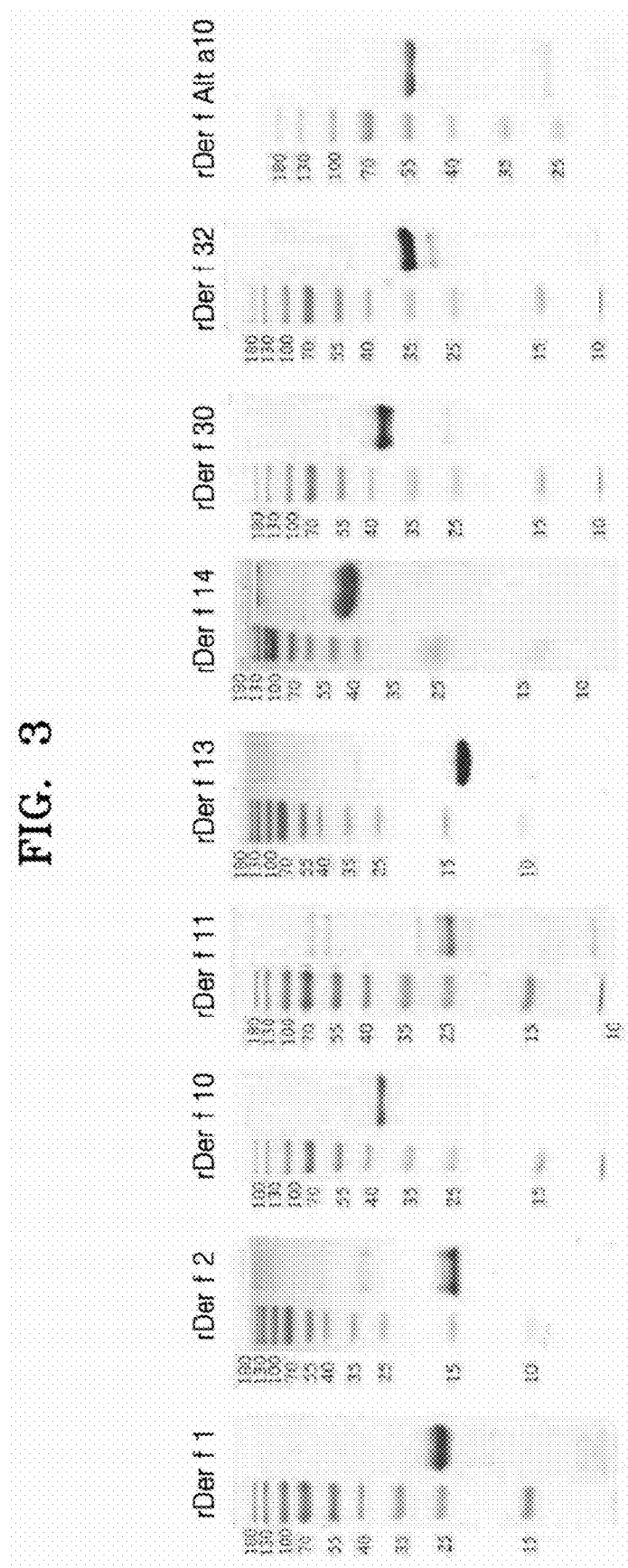
FIG. 3 shows results of examining recombinant allergens of *Dermatophagoides farinae*.

Recombinant Der f 1, Der f 2, and Der f 10 were prepared as follows. A mutant Der f 1 pro-form having a histidine tag at the C-terminus was prepared in a *Pichia* expression system. Der f 2 derived from inclusion body and Der f 10 derived from a soluble fraction were expressed in *E. coli*, and purified using a Ni-nitrilotriacetic acid (NTA) resin (Qiagen, Valencia, Calif.). Der f 14 and Der f 11 were prepared as peptide fragments. Since peptide fragments of Der f 14 degraded by protease are more allergenic than non-fragmented Der f 14, partial C-terminal sequences of Der f 14 were prepared and expressed. Der f 11 was prepared by expressing Der f 11 peptide fragment which is known as an immunodominant peptide. In order to clone Der f 11 peptide fragment, Der f 13, Der f 14 peptide fragment, Der f 30, Der f 32, and Der f Alt a 10, total RNA was isolated from mites, and the isolated total RNA was used to synthesize cDNA. Based on sequences registered in GenBank, oligonucleotide primer sets specific to respective allergens were prepared, and the primer sets and the synthesized cDNA were used to amplify coding regions of the respective allergens by polymerase chain reaction (PCR). Sequences of the oligonucleotide primer sets for amplification and expression, and host cells, which were used in the cloning of the allergens, are shown in Table 3 below. In Table 3, * represents the peptide fragment. cDNA fragment of each allergen was ligated with a pEXP5NT TOPO vector (Invitrogen, Carlsbad, Calif.), and this vector was transformed into *E. coli* BL21(DE3) or *Pichia*. 1 mM isopropyl-1-thio- β-D-galactopyranoside was added to induce expression of the recombinant allergens. Subsequently, Ni-NTA resin (Qiagen) was used to purify the recombinant proteins. All recombinant allergens, excluding Der f 11 peptide fragment, were separated from inclusion bodies, and separated on a SDS-polyacrylamide gel under reducing conditions, and protein concentrations were quantified by Bradford assay. SDS-PAGE results of the recombinant mite allergens prepared in this study are shown in FIG. 3. rDer f 1 is cysteine protease and has about 27 kDa. rDer f 2 is a NPC2 family and has about 15 kDa. rDer f 10 is tropomyosin and has about 37 kDa. rDer f 11 is a fragment of paramyosin and has about 98 kDa. rDer f 13 is a fatty acid-binding protein and has about 15 kDa. rDer f 14 is a fragment of apolipophorin and has about 177 kDa. rDer f 30 is ferritin and has about 16 kDa. rDer f 32 is secreted inorganic pyrophosphatase and has about 35 kDa. rDer f Alt a 10 is aldehyde dehydrogenase and has a homology with a fungus allergen Alt a 10 and has about 54 kDa.

showed a significant correlation with Der p 2 IgE titers detected by ImmunoCAP ($R^2=0.82$).

7. Sensitization Profiling of *D. farinae* Component Allergens

2 μg/ml of the recombinant protein was dissolved in a 0.05 M carbonate buffer solution at pH 9.6, and coated onto a microplate, followed by incubation at 4° C. overnight. The incubated plate was washed with a phosphate buffered saline solution containing 0.05% Tween 20 (PBST), and the plate was incubated with PBST containing 3% skim milk to block non-specific binding. A serum sample was diluted with PBST containing 1% bovine serum albumin at 1:4, and dispensed into the plate, followed by incubation for 1 hour. Subsequently, biotin-conjugated goat anti-human IgE (1:1,000) (Vector, Burlingame, Calif.) and streptavidin peroxidase (1:1,000) (Sigma-Aldrich) were added to detect IgE antibody. Subsequently, 3,3',5,5'-tetramethylbenzidine (Kirkegaard and Perry Laboratories, Gaithersburg, Md.) was used for color development. 0.5 M $H_2SO_4$ was added and

TABLE 3

| Allergen | Host cell | Primer | Sequence 5'-3' |
|---|---|---|---|
| rDer f 1 | Pichia | Forward | 5'-CTCGAGCGTCCAGCTTCAATCAAAACT-3' (SEQ ID NO: 22) |
| | | Reverse | 5'-GGCCGCTTAGTGATGGTGATGGTGATGCGCG CCGCGTGATGGTG-3' (SEQ ID NO: 23) |
| rDer f 2 | E.coli | Forward | 5'-GATCAAGTCGATGTTAAAG-3' (SEQ ID NO: 24) |
| | | Reverse | 5'-TCAAACAATGTTTTTTGT-3' (SEQ ID NO: 25) |
| rDer f 10 | E.coli | Forward | 5'-ATGGAGGCCATCAAGAAA-3' (SEQ ID NO: 26) |
| | | Reverse | 5'-CTGTCTGCGTAATATGAAAG-3' (SEQ ID NO: 27) |
| rDer f 11* | E.coli | Forward | 5'-cacattgaatcggaagaaacg-3' (SEQ ID NO: 28) |
| | | Reverse | 5'-TgATTCTAATTCCACTTCCAA-3' (SEQ ID NO: 29) |
| | E.coli | Forward | 5'-ATggCAAgCATTgAAggTAA-3' (SEQ ID NO: 30) |
| | | Reverse | 5'-TTAgATTCgTTTATATgTTC-3' (SEQ ID NO: 31) |
| rDer f 13 | E.coli | Forward | 5'-atggatccgtcaacattgag-3' (SEQ ID NO: 32) |
| | | Reverse | 5'-TCAgTTgTCTTCgACgATgAAATT-3' (SEQ ID NO: 33) |
| rDer f 14* | E.coli | Forward | 5'-ATggCTgCTAATCCTgAATC-3' (SEQ ID NO: 34) |
| | | Reverse | 5'-TTACgATgAATgCAATgTATgAC-3' (SEQ ID NO: 35) |
| rDer f 30 | E.coli | Forward | 5'-ATgTCTACTACAAATTATTC-3' (SEQ ID NO: 36) |
| | | Reverse | 5'-TTAgATCAATTTAACATgATgCC-3' (SEQ ID NO: 37) |
| rDer f 32 | Pichia | Forward | 5'-ATggCCCAAgTggAAgTAAAA-3' (SEQ ID NO: 38) |
| | | Reverse | 5'-CTAATTTAAATTCgAATTTTTATTC-3' (SEQ ID NO: 39) |
| rDer f Alt a 10 | E.coli | Forward | 5'-atggcccaagtggaagtaaaatatac-3' (SEQ ID NO: 40) |
| | | Reverse | 5'-CTAATTTAAATTCgAATTTTTATTC-3' (SEQ ID NO: 41) |

6. Protein Profiling of *D. farinae* Component Allergens

Serum sIgE was detected using ImmunoCAP (ThermoFisher Scientific, Uppsala, Sweden). IgE titers higher than 0.35 kUA/L were considered positive. sIgE to total *D. farinae* extract and sIgE to Der p 1, Der p 2, and Der p 10 which are commercially available mite component allergens were measured.

Figure 4:
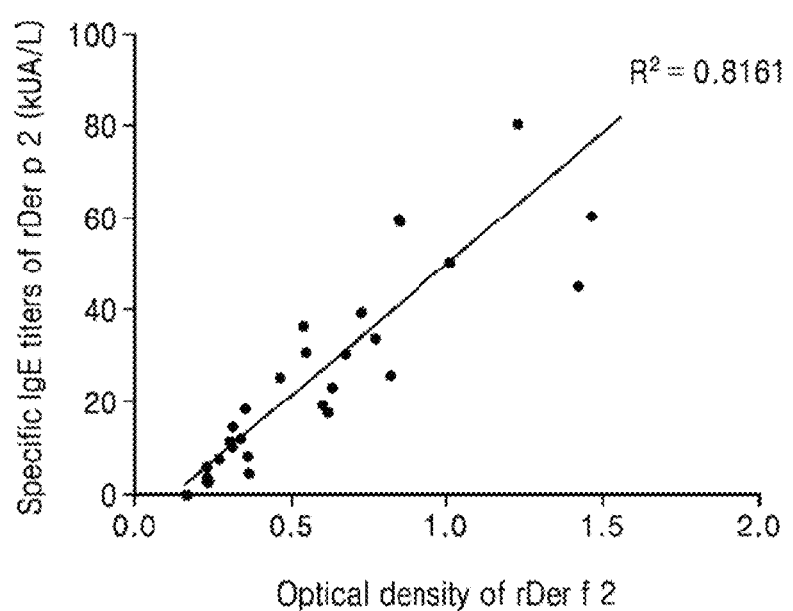
FIG. 4 shows results of comparing IgE reactivities to mite allergens by ELISA and ImmunoCAP.

To compare IgE reactivities to the component allergens, ELISA and ImmunoCAP were performed. Since the recombinant component allergens of *D. farinae* cannot be used in ImmunoCAP, Der p 2 was used. FIG. 4 shows data showing a comparison of IgE reactivities to mite allergens in ELISA and ImmunoCAP. As shown in FIG. 4, Der f 2 ELISA data absorbance at 450 nm was measured. Mean absorbance value of negative controls and standard deviations of triplicate experiments were determined as cut-off value.

Figure 5A:
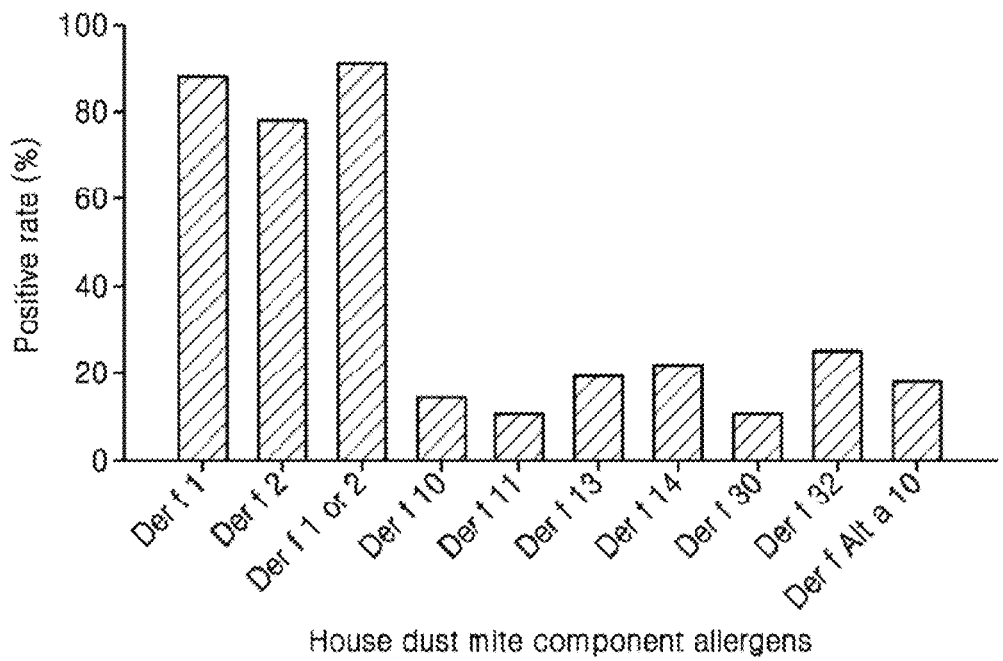
FIGS. 5A and 5B show sensitization profiles of all allergic disease patients and allergic respiratory disease or skin allergic disease patient groups with respect to house dust mite component allergens.
Figure 5B:
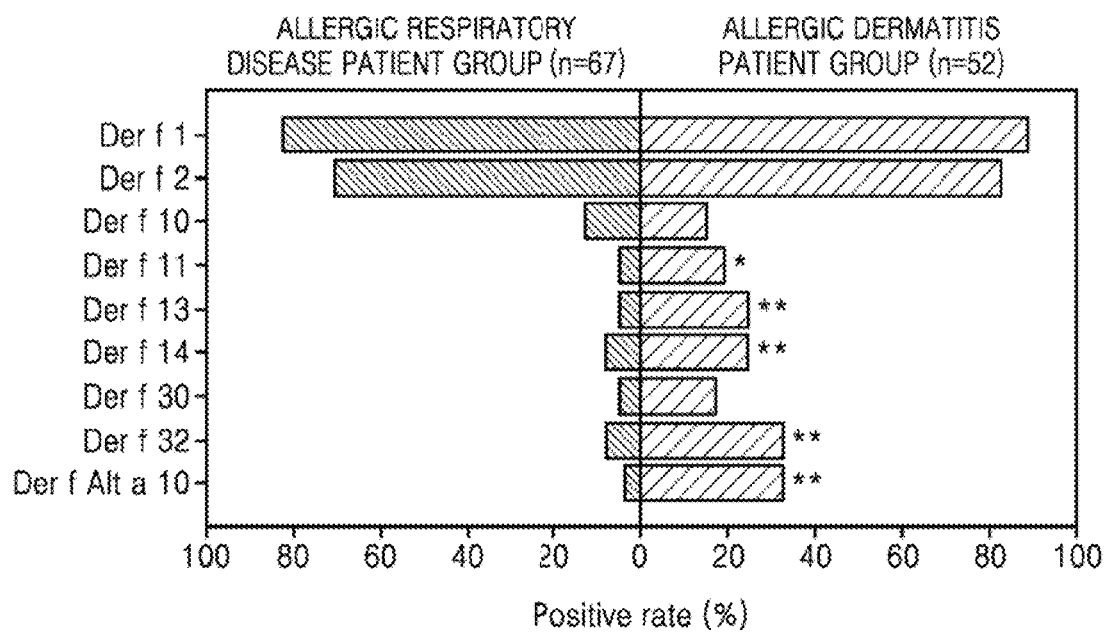

IgE reactivities of the respective component allergens are shown in FIG. 5. As shown in FIG. 5A, about 91% of the patients of Group 1 (allergic respiratory disease patient group) or Group 2 (allergic dermatitis patient group) were sensitized to major allergens. Only 14 patients (8.8%) were sensitized to minor allergens. Sensitization profiles of the respective groups are shown in FIG. 5B. The atopic dermatitis patient group showed higher sensitization rates of Der f 11, Der f 13, Der f 14, Der f 32, and Der f Alt 10 than the allergic respiratory disease patient group.

Figure 6A:
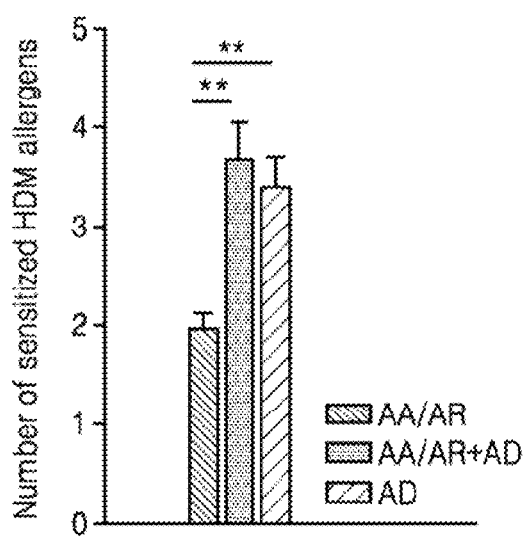
FIGS. 6A and 6B show the distribution of the number of sensitized component allergens in allergic respiratory disease patients and dermatitis patients.
Figure 6B:
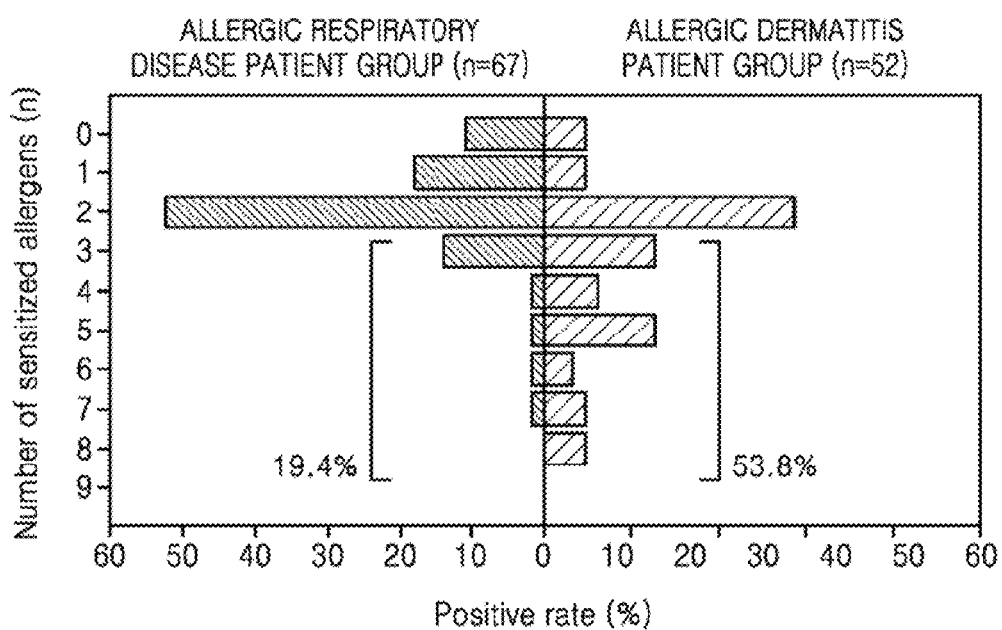
Figure 7:
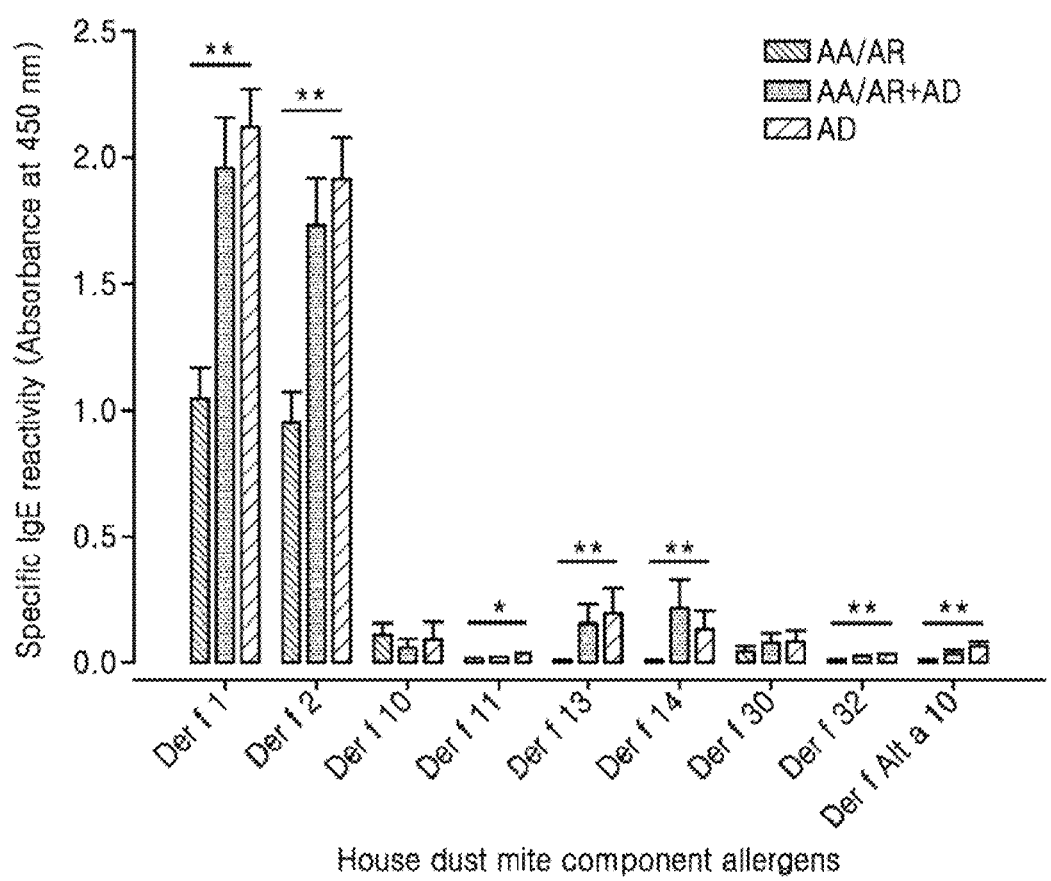
FIG. 7 shows IgE reactivities specific to component allergens in the respective disease groups.
Figure 8:
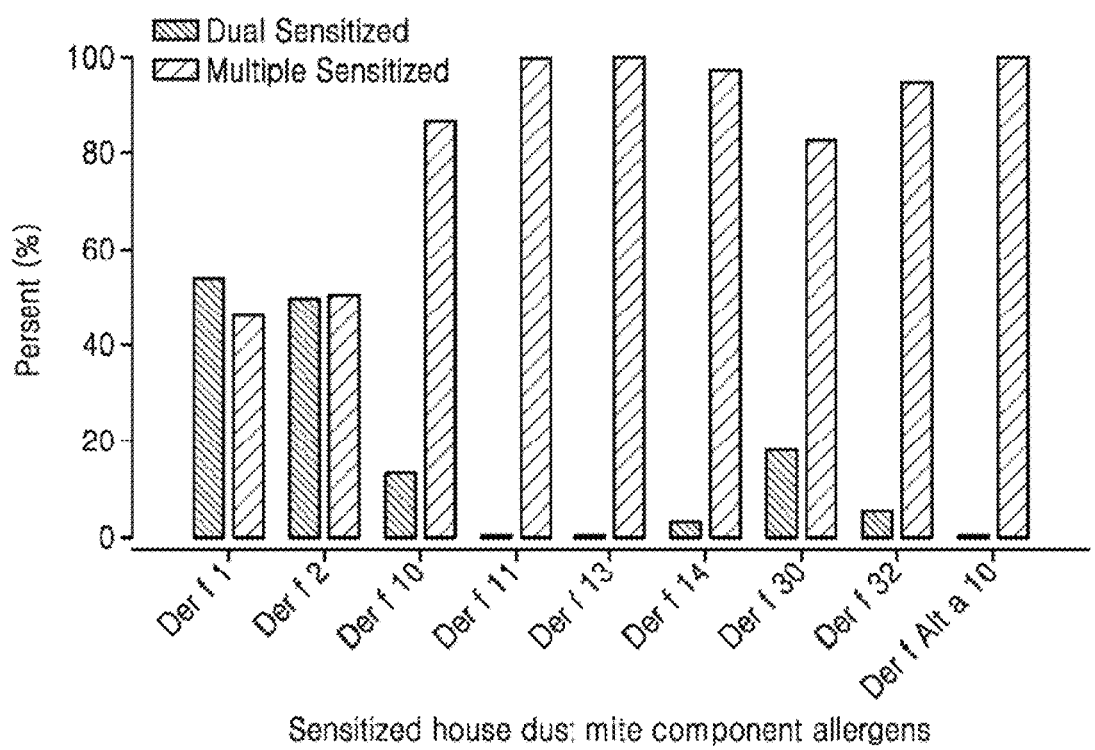
FIG. 8 show percent (%) of dual sensitizer or multiple sensitizer to sensitized house dust mites component allergens.

As shown in FIG. 6, the number of sensitized allergens was different between the groups. The allergic dermatitis patients tended to be sensitized to various mite component allergens. As shown in FIG. 6A, the atopic dermatitis-accompanying allergic asthma or allergic rhinitis patients showed the largest number of sensitized allergens. As shown in FIG. 6B, about 80.6% patients of the allergic respiratory disease patient group were sensitized to two kinds of allergens. However, about 54% of the atopic dermatitis patients were sensitized to three to five kinds of allergens. The atopic dermatitis patient group showed the highest optical density of the major allergen (Der f 1 or Der f 2), which was measured by ELISA. Further, the atopic dermatitis patient group showed the highest IgE reactivities of Der f 11, 13, 14, 32, and Alt a 10. Patients sensitized to minor allergy antigens tended to be sensitized to various HDM component allergens. Referring to FIG. 8, it was found that Der f 11, Der f 13, and Der f Alt a 10 antigens (sensitizers) were all multiple antigens.

TABLE 4

| | Total (n = 160) | AA/AR (n = 67) | AA/ AR + AD (n = 41) | AD (n = 52) | P value |
|---|---|---|---|---|---|
| Der f 1, n(%) | 141(88.1%) | 55(82.1%) | 40(97.6%) | 46(88.5%) | 0.054 |
| Der f 2, n(%) | 125(78.1%) | 47(70.1%) | 35(85.4%) | 43(82.7%) | 0.112 |
| Der f 1 or 2, n(%) | 146(91.3%) | 57(85.1%) | 40(97.6%) | 49(94.2%) | 0.070 |
| Der f 10, n(%) | 23(14.4%) | 8(11.9%) | 7(17.1%) | 8(15.4%) | 0.738 |
| Der f 11, n(%) | 17(10.6%) | 3(4.5%) | 4(9.8%) | 10(19.2%) | 0.034 |
| Der f 13, n(%) | 31(19.4%) | 3(4.5%) | 15(36.6%) | 13(25.0%) | <0.001 |
| Der f 14, n(%) | 35(21.9%) | 5(7.5%) | 17(41.5%) | 13(25.0%) | <0.001 |
| Der f 30, n(%) | 17(10.6%) | 3(4.5%) | 5(12.2%) | 9(17.3%) | 0.074 |
| Der f 32, n(%) | 40(25.0%) | 5(7.5%) | 18(43.9%) | 17(32.7%) | <0.001 |
| Der f Alt a 10, n(%) | 29(18.1%) | 2(3.0%) | 10(24.4%) | 17(32.7%) | <0.001 |

8. Statistical Analysis

The above results were analyzed using IBM SPSS Statistics (IBM Corp Armonk, N.Y.) for Windows Version 23.0. For comparisons of parameters, Kruskal-Wallis test, Fisher's exact test, or Pearson's chi-squared test was used. Non-parametric continuous data were analyzed by Kruskal-Wallis test, and categorical data were analyzed by Fisher's exact test or Pearson's chi-squared test. For multiple comparisons between groups, Dunn test was performed after Kruskal-Wallis test. $P<0.05$ was considered statistically significant.

In this study, proteome and allergenome of house dust mite were analyzed, and sensitization profiles of allergic respiratory disease patients and allergic dermatitis (atopic dermatitis) patients were investigated. As a result, allergic respiratory disease patients were sensitized to Der f 1 and Der f 2 which are the major allergens. In contrast, patients with allergic dermatitis symptoms showed multiple sensitization to minor allergens as well as major allergens. The composition for diagnosing allergic diseases to mites includes Der f 11, Der f 13, Der f 14, Der f 32, Der f Alt a 10, or a combination thereof, and therefore, atopic dermatitis patient group may be sensitized to an allergen of Der f 11, Der f 13, Der f 14, Der f 32, Der f Alt a 10, or a combination thereof, and the atopic dermatitis patient group showed about 2 times or higher, about 2.5 times or higher, about 3 times or higher, about 3.5 times or higher, about 4 times or higher, about 4.5 times or higher, or about 5 times or higher sensitization rates to the allergen than the patient group only with allergic asthma or allergic rhinitis, or a normal group. Further, allergic dermatitis patients showed IgE sensitization to various mite component allergens and high sIgE reactivities.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of diagnosing and treating allergic dermatitis in a subject comprising:

isolating a biological sample from the subject;

detecting the presence of IgE antibodies in the biological sample to Der f 11, Der f 13, Der f 14, Der f 32, and Der f Alt a 10;

diagnosing the subject as having atopic dermatitis responsive to the biological sample comprising IgE antibodies to Der f 11, Der f 13, Der f 14, Der f 32, and Der f Alt a 10; and treating the subject diagnosed as having atopic dermatitis by administering an effective amount of Der f 11, Der f 13, Der f 14, Der f 32, and Der f Alt a 10 allergens to the subject, wherein the Der f 11, Der f 13, Der f 14, Der f 32, and Der f Alt a 10 allergens comprise amino acid sequences selected from the group consisting of SEQ ID NOs: 1, 3, 5, 7, and 9.

2. The method of claim 1, further comprising detecting the presence of IgE antibodies to Der f 1, Der f 2, Der f 10, Der f 30, or a combination thereof, in the biological sample.

3. The method of claim 2, wherein the detecting is performed by immunoassay;

wherein the immunoassay comprises Der f 1, Der f 2, Der f 10, and Der f 30 allergens, or a combination thereof; and wherein the Der f 1, Der f 2, Der f 10, and Der f 30 allergens comprise amino acid sequences selected from the group consisting of SEQ ID NOs: 11, 13, 15, and 17.

4. The method of claim 1, wherein the detecting is performed by immunoassay;

wherein the immunoassay comprises Der f 11, Der f 13, Der f 14, Der f 32, and Der f Alt a 10 allergens; and wherein the Der f 11, Der f 13, Der f 14, Der f 32, Der f Alt a 10 allergens comprise amino acid sequences selected from the group consisting of SEQ ID NOs: 1, 3, 5, 7, and 9.

5. The method of claim 2, further comprising administering an effective amount of Der f 1, Der f 2, Der f 10, and Der f 30 allergens, or a combination thereof, to the subject.

6. The method of claim 5, wherein the Der f 1, Der f 2, Der f 10, and Der f 30 allergens comprise amino acid sequences selected from the group consisting of SEQ ID NOs: 11, 13, 15, and 17.

* * * * *